(12) United States Patent
Wang et al.

(10) Patent No.: US 9,171,220 B2
(45) Date of Patent: Oct. 27, 2015

(54) APPARATUS AND METHOD FOR TRACKING CONTOUR OF MOVING OBJECT, AND APPARATUS AND METHOD FOR ANALYZING MYOCARDIAL MOTION

(75) Inventors: Yanhua Wang, Beijing (CN); Chao Cong, Beijing (CN); Yanli Wang, Beijing (CN); Shaobin Wang, Beijing (CN); Qiuying Dong, Beijing (CN)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 265 days.

(21) Appl. No.: 13/553,308

(22) Filed: Jul. 19, 2012

(65) Prior Publication Data

US 2013/0182935 A1    Jul. 18, 2013

(30) Foreign Application Priority Data

Jul. 19, 2011   (CN) .......................... 2011 1 0209868

(51) Int. Cl.
| | |
|---|---|
| G06K 9/00 | (2006.01) |
| G06K 9/32 | (2006.01) |
| G06T 7/20 | (2006.01) |
| A61B 6/00 | (2006.01) |
| A61B 8/08 | (2006.01) |

(Continued)

(52) U.S. Cl.
CPC .............. *G06K 9/3233* (2013.01); *A61B 6/503* (2013.01); *A61B 6/5217* (2013.01); *A61B 8/0883* (2013.01); *A61B 8/5223* (2013.01); *G06T 7/2033* (2013.01); *A61B 5/055* (2013.01); *A61B 6/032* (2013.01); *A61B 6/037* (2013.01); *G06T 2207/20168* (2013.01); *G06T 2207/30048* (2013.01)

(58) Field of Classification Search
None
See application file for complete search history.

(56) References Cited

U.S. PATENT DOCUMENTS 5,239,591 A * 8/1993 Ranganath ..................... 382/128
5,999,651 A * 12/1999 Chang et al. .................. 382/215

(Continued)

FOREIGN PATENT DOCUMENTS

| EP | 1 876 567 A1 | 1/2008 |
|---|---|---|
| EP | 2 434 454 A2 | 3/2012 |
| WO | WO 2007/138522 A1 | 12/2007 |

OTHER PUBLICATIONS

Partial European Search Report issued Nov. 5, 2012 in Patent Application No. 12177094.5.

(Continued)

*Primary Examiner* — Hadi Akhavannik
(74) *Attorney, Agent, or Firm* — Oblon, McClelland, Maier & Neustadt, L.L.P.

(57) ABSTRACT

A moving object contour tracking apparatus includes a contour tracking section for performing, by taking an initial contour of the moving object in a predetermined image slice as a starting contour, contour tracking in a first time direction to acquire a first contour of the moving object and contour tracking in a second time direction to acquire a second contour of the moving object in each image slice; a contour comparison section for calculating, in the predetermined image slice, a similarity between the first contour and the initial contour and a similarity between the second contour and the initial contour; and a contour correction section for taking the contours in the image slices that are acquired in a contour tracking direction corresponding to the greater one of the two similarities as the contours of the moving object in the respective image slices.

11 Claims, 23 Drawing Sheets

(51) Int. Cl.
*A61B 6/03* (2006.01)
*A61B 5/055* (2006.01)

(56) References Cited

U.S. PATENT DOCUMENTS

| | | |
|---|---|---|
| 6,368,277 B1 | 4/2002 | Mao et al. |
| 7,558,402 B2 | 7/2009 | Zhou et al. |
| 7,577,281 B2 | 8/2009 | Nishiura |
| 2003/0153823 A1 | 8/2003 | Geiser et al. |
| 2008/0015428 A1* | 1/2008 | Epstein et al. ............ 600/410 |
| 2008/0304730 A1 | 12/2008 | Abe |
| 2009/0131788 A1 | 5/2009 | Settlemier et al. |
| 2009/0232371 A1 | 9/2009 | Jolly |
| 2012/0078097 A1 | 3/2012 | Wang et al. |

OTHER PUBLICATIONS

Paulo F. U. Gotardo et al., "A New Deformable Model for Boundary Tracking in Cardiac MRI and Its Application to the Detection of Intra-Ventricular Dyssynchrony", Conference on Computer Vision and Patern Recognition, 2006 IEEE Computer Society, XP-010923032, vol. 1, Jun. 17, 2006, 8 pages.

J. Cho, "Sequential Cardiac Segmentation by Seed Contour Tracking", Electronics Letters, IEE Stevenage, XP-006022935, vol. 40, No. 23, Nov. 11, 2004, 2 pages.

The Extended European Search Report issued Mar. 25, 2013, in Application no. / Patent No. 12177094.5-1906-2549436.

Thomas E. Stanley, et al., "Quantitative Analysis of Transesophageal Echocardiograms for the Intraoperative Setting: Clinical Need and Initial Experience", IEEE Engineering in Medicine & Biology Society 11th Annual International Conference, vol. 11, (Images of the Twenty First Century ), Nov. 9, 1989, XP000129522, 3 pages.

* cited by examiner

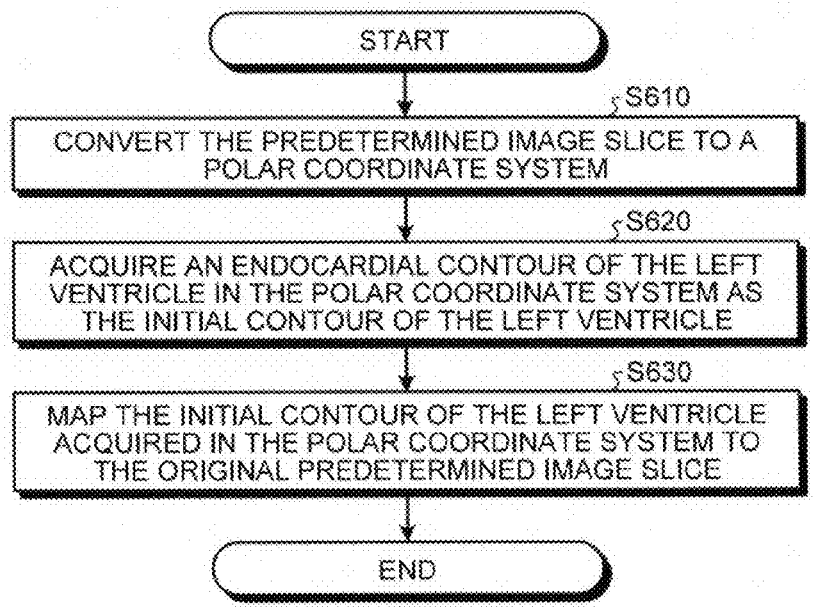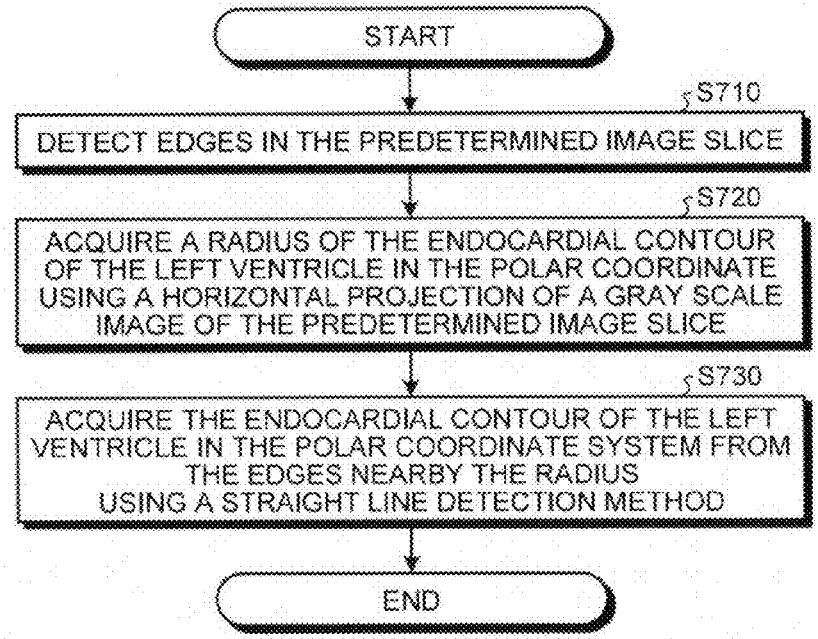

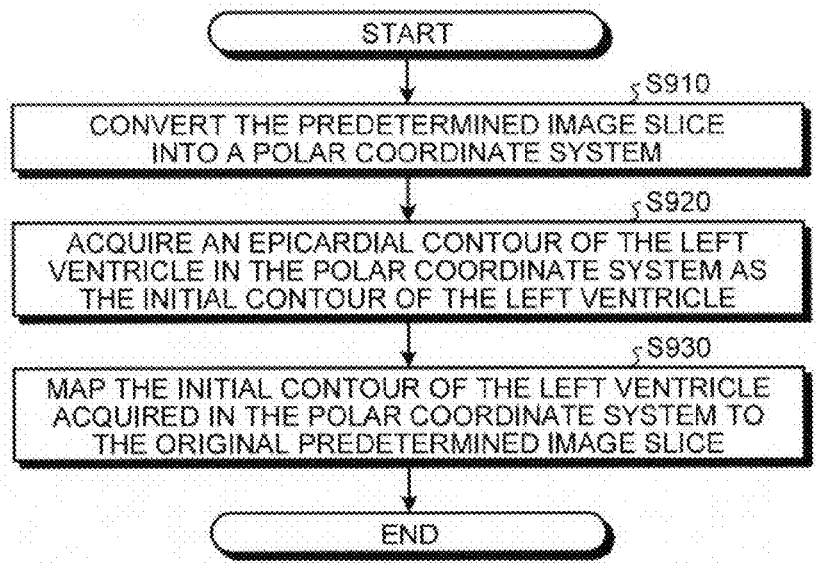
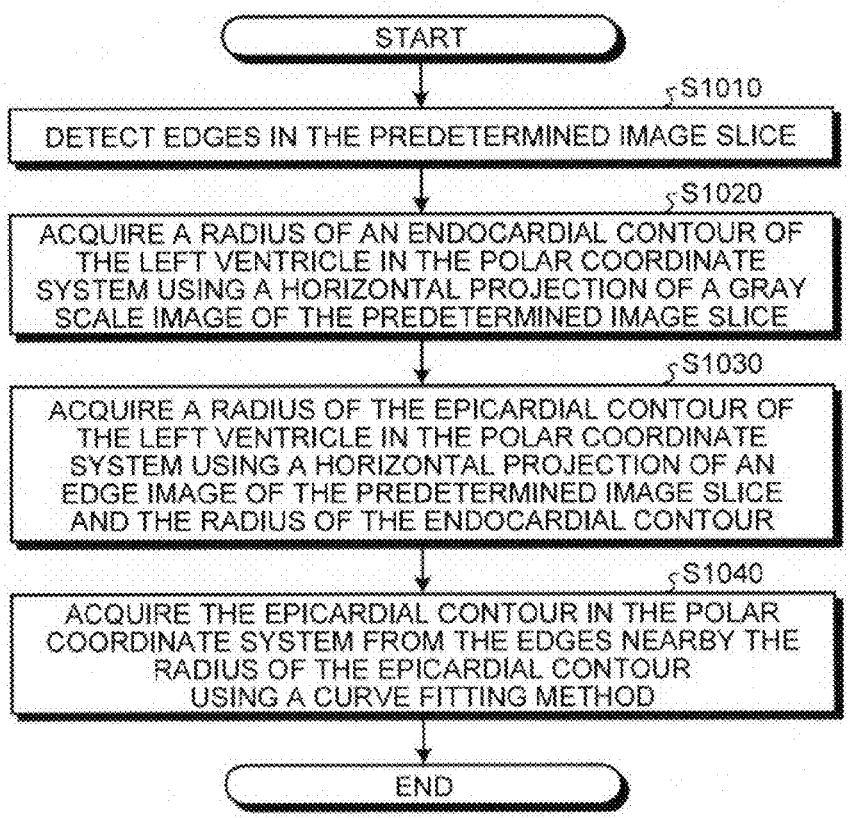

APPARATUS AND METHOD FOR TRACKING
CONTOUR OF MOVING OBJECT, AND
APPARATUS AND METHOD FOR
ANALYZING MYOCARDIAL MOTION

CROSS-REFERENCE TO RELATED
APPLICATIONS

This application is based upon and claims the benefit of priority from Chinese Patent Application No. 201110209868.9, filed on Jul. 19, 2011, the entire contents of which are incorporated herein by reference.

FIELD

The present invention relates to the field of computer vision and more particularly, to a apparatus and method for tracking contour of moving object, and apparatus and method for analyzing myocardial motion.

BACKGROUND

The contour extraction of a moving object, especially of a deforming object, is a challenge in the field of computer vision. In actual applications, for example, in the medial field, the contour extraction of an organ or a part of an organ from a three-dimensional image time series acquired by a computed tomography (CT) apparatus, a Magnetic Resonance Imaging (MRI) apparatus, an ultrasonic (UL) apparatus and the like is beneficial to subsequent measurement on various parameters of the organ.

Some conventional moving object contour extraction methods extract the contour of a moving object separately from each phase, which may lead to an error extraction in a specific phase.

Some other motion tracking based methods which track the contour of a moving object in a motion period of the moving object may produce an error accumulation, resulting in a significant difference between the acquired contour in the first phase and that in the last phase.

In addition, in the field of cardiology, a nuclear magnetic resonance imaging technology is typically used to provide a three-dimensional image time series (3D+T) of a heart. Doctors are highly interested in recognizing a ventricle, an endocardium, an epicardium and analyzing the motion of a heart. The contours of the recognized ventricle, endocardium and epicardium can be used to measure a ventricular blood volume (ejection fraction), the motion of a ventricular wall, a characteristic of wall thickness and the like at different stages of a cardiac cycle. The motion vector of a myocardium can be used to calculate parameters of the myocardium, such as strain and strain force. Left ventricle (LV) is of great importance because it pumps oxygenated blood to various issues of a body from the heart.

There have been developed many medical motion image processing techniques to quantify myocardial motion, including spot tracking, myocardial tagging, registering and propagation contours with initial contour of myocardium, and various myocardium segmentation methods.

BRIEF DESCRIPTION OF THE DRAWINGS

The present invention will be better understood by reference to the following description taken in conjunction with accompanying drawings in which identical or like sections are designated with identical or like reference signs designate. The accompanying drawings, together with the detailed description below, are incorporated into and form a part of the specification, and serve to further illustrate, by way of example, preferred embodiments of the present invention and to explain the principle and advantages of the present invention. In the accompanying drawings:

FIG. 6 is a schematic flow chart illustrating a method for acquiring an initial contour of a left ventricle according to an embodiment of the present invention;

FIG. 7 shows a schematic flow chart illustrating the acquiring of an endocardial contour of a left ventricle according to an embodiment of the present invention;

FIG. 9 is a schematic flow chart illustrating the acquiring of an initial contour of a left ventricle according to another embodiment of the present invention;

FIG. 10 is a schematic flow chart illustrating the acquiring of an epicardial contour of a left ventricle according to an embodiment of the present invention;

DETAILED DESCRIPTION

Figure 1:
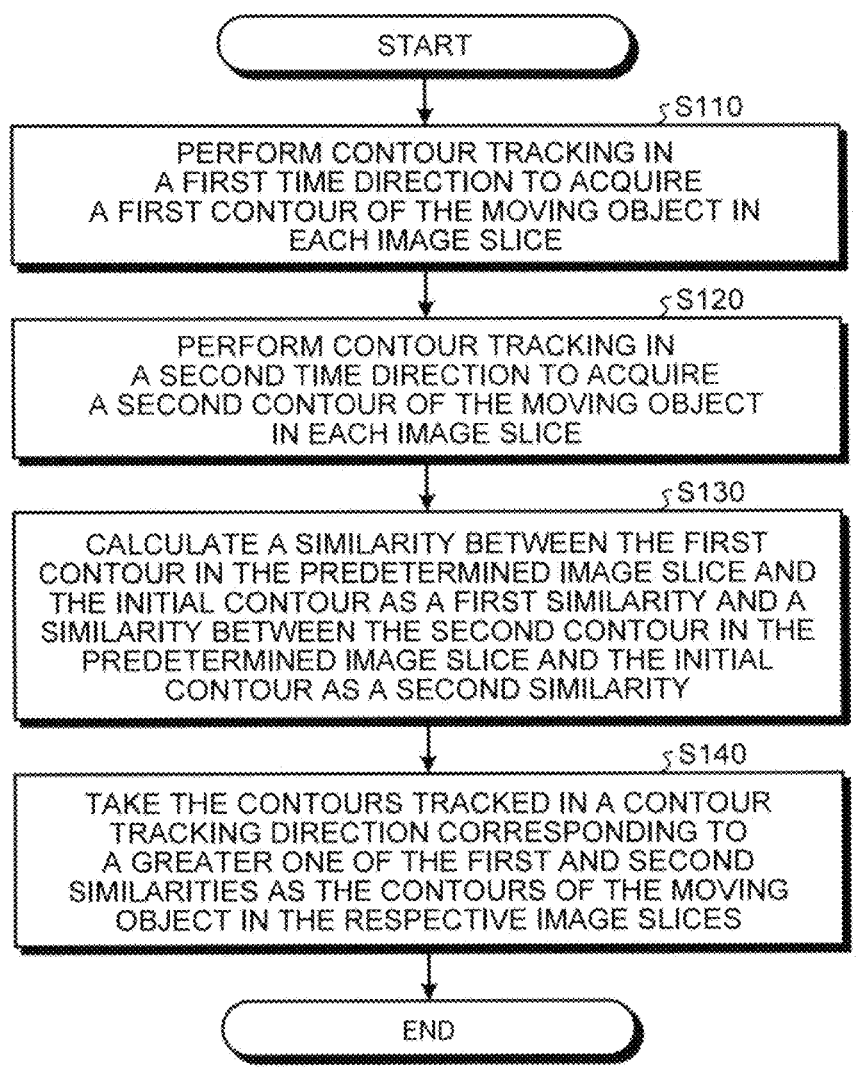
FIG. 1 is a schematic flow chart illustrating a moving object contour tracking method according to an embodiment of the present invention.

According to an embodiment, A moving object contour tracking apparatus for tracking a contour of a periodically deforming object in an image slice time series, the image slice time series comprising a plurality of image slices acquired at a plurality of time points in a motion period of the moving object, the moving object contour tracking apparatus includes a contour tracking section, a contour comparison section and a contour correction section. The contour tracking section configured to perform, by taking an initial contour of the moving object in a predetermined image slice of the image slice time series as a starting contour, contour tracking in the image slice time series in a first time direction to acquire a first contour of the moving object in each image slice of the image slice time series, and perform, by taking the initial contour as a starting contour, contour tracking in the image slice time series in a second time direction to acquire a second contour of the moving object in each image slice of the image slice time series. The contour comparison section configured to calculate a similarity between the first contour of the moving object in the predetermined image slice and the initial contour as a first similarity and a similarity between the second contour of the moving object in the predetermined image slice and the initial contour as a second similarity. The contour correction section configured to take the contours in the image slices tracked by the contour tracking section in a contour tracking direction corresponding to a greater one of the first and second similarities as the contours of the moving object in the respective image slices.

The following presents a simplified summary of the present invention to provide a basic understanding of some aspects of the present invention. It should be understood that the summary is not an exhaustive summary of the present invention. It is not intended to identify the key or critical parts of the present invention, nor intended to limit the scope of the present invention. It only aims to present some concepts in a simplified form as a prelude to the more detailed description that is to be discussed later.

It is an object of the present invention to provide a moving object contour tracking method and apparatus for extracting a contour of a moving object accurately from an image slice time series. It is another object of the present invention to provide a moving object contour tracking method and apparatus for extracting a moving object contour accurately from a three-dimensional image time series. It is a further object of the present invention to provide a myocardial motion analysis method and apparatus for analyzing the motion of a myocardium of a left ventricle stably from a medical image slice time series. It is a still further object of the present invention to provide a myocardial motion analysis method and apparatus for analyzing the motion of a myocardium of a left ventricle stably from a three-dimensional medical image time series.

In accordance with an aspect of the present invention, there is provided a moving object contour tracking method for tracking a contour of a periodically deforming object in an image slice time series, the image slice time series comprising a plurality of image slices acquired at a plurality of time points in a motion period of the moving object. The method includes: performing, by taking an initial contour of the moving object in a predetermined image slice of the image slice time series as a starting contour, contour tracking in the image slice time series in a first time direction to acquire a first contour of the moving object in each image slice of the image slice time series, wherein a last image slice is taken as the previous image slice of a first image slice in the first time direction; performing, by taking the initial contour as a starting contour, contour tracking in the image slice time series in a second time direction to acquire a second contour of the moving object in each image slice of the image slice time series, wherein a last image slice is taken as the previous image slice of a first image slice in the second time direction; calculating a similarity between the first contour of the moving object in the predetermined image slice and the initial contour as a first similarity and a similarity between the second contour of the moving object in the predetermined image slice and the initial contour as a second similarity; and taking the contours in the image slices tracked by the contour tracking section in a contour tracking direction corresponding to a greater one of the first and second similarities as the contours of the moving object in the respective image slices.

In accordance with another aspect of the present invention, there is provided a moving object contour tracking method for tracking the contour of a periodically deforming moving object in a three-dimensional image time series, the three-dimensional image time series comprising a plurality of three-dimensional images acquired at a plurality of time points in a motion period of the moving object, each of the three-dimensional images consisting of a plurality of parallel two-dimensional image slices, and the two-dimensional image slices located at the same location in the plurality of three-dimensional images forming an image slice time series. The method includes: tracking a contour of the moving object in each image slice time series using the moving object contour tracking method according to the above aspect of the present invention. The contours of the moving object in the plurality of two-dimensional image slices at the same time point form a three-dimensional contour of the moving object at this time point.

In accordance with another aspect of the present invention, there is provided a myocardial motion analysis method for analyzing a motion of a myocardium of a left ventricle in a medical image slice time series, the medical image slice time series comprising a plurality of image slices acquired with respect to a section of the left ventricle intersected with a long axis of the left ventricle at a plurality of time points in a cardiac cycle. The method includes: acquiring an endocardial contour and an epicardial contour of the left ventricle in each image slice; configuring contour points on the endocardial contour and the epicardial contour in a reference image slice of the image slice time series as a plurality of point linking pairs, each point linking pair comprising a contour point on the endocardial contour and a contour point on the epicardial contour, and the two contour pints of each point linking pair being located on the same normal of a reference contour of a left ventricle wall in the reference image slice; determining locations of each point linking pair in other image slices of the image slice time series; and calculating, according to the locations of the plurality of point linking pairs in adjacent image slices of the image slice time series, a motion vector of the myocardium of the left ventricle between the adjacent image slices, the myocardium being defined by the endocardial contour and the epicardial contour.

In accordance with another aspect of the present invention, there is provided a myocardial motion analysis method for analyzing a motion of a myocardium of a left ventricle in a three-dimensional medical image time series, the three-dimensional medical image time series comprising a plurality of three-dimensional images acquired at a plurality of time points in a cardiac cycle, each of the three-dimensional images consisting of a plurality of parallel two-dimensional image slices that are intersected with a long axis of the left ventricle, and the two-dimensional image slices located at the same location in the three-dimensional images forming an image slice time series. The method includes: analyzing the motion of the myocardium of the left ventricle in each medical image slice time series using the myocardial motion analysis method according to the above aspect of the present invention. The motions of the myocardium in the plurality of two-dimensional image slices at the same time point form a motion of the left ventricle at this time point.

In accordance with another aspect of the present invention, there is provided a moving object contour tracking apparatus for tracking a contour of a periodically deforming object in an image slice time series, the image slice time series comprising a plurality of image slices acquired at a plurality of time points in a motion period of the moving object. The apparatus includes: a contour tracking section configured to perform, by taking an initial contour of the moving object in a predetermined image slice of the image slice time series as a starting contour, contour tracking in the image slice time series in a first time direction to acquire a first contour of the moving object in each image slice of the image slice time series, wherein a last image slice is taken as the previous image slice of a first image slice in the first time direction, and perform, by taking the initial contour as a starting contour, contour tracking in the image slice time series in a second time direction to acquire a second contour of the moving object in each image slice of the image slice time series, wherein a last image slice is taken as the previous image slice of a first image slice in the second time direction; a contour comparison section configured to calculate a similarity between the first contour of the moving object in the predetermined image slice and the initial contour as a first similarity and a similarity between the second contour of the moving object in the predetermined image slice and the initial contour as a second similarity; and a contour correction section configured to take the contours in the image slices tracked by the contour tracking section in a contour tracking direction corresponding to a greater one of the first and second similarities as the contours of the moving object in the respective image slices.

In accordance with another aspect of the present invention, there is provided a moving object contour tracking apparatus for tracking a contour of a periodically deforming moving object in a three-dimensional image time series, the three-dimensional image time series comprising a plurality of three-dimensional images acquired at a plurality of time points in a motion period of the moving object, each of the three-dimensional images consisting of a plurality of parallel two-dimensional image slices, and the two-dimensional image slices located at the same location in the plurality of three-dimensional images forming an image slice time series. The apparatus includes: a tracking section implemented by the moving object contour tracking apparatus according to the above aspect of the present invention and configured to track a contour of the moving object in each image slice time series. The contours of the moving object in the plurality of two-dimensional image slices at the same time point form a three-dimensional contour of the moving object at this time point.

In accordance with another aspect of the present invention, there is provided a myocardial motion analysis apparatus for analyzing a motion of a myocardium of a left ventricle in a medical image slice time series, the medical image slice time series comprising a plurality of image slices acquired with respect to a section of the left ventricle intersected with a long axis of the left ventricle at a plurality of time points in a cardiac cycle. The apparatus includes: a contour acquisition section configured to acquire an endocardial contour and an epicardial contour of the left ventricle in each image slice; a point linking pair configuration section configured to configure contour points on the endocardial contour and the epicardial contour in a reference image slice of the image slice time series as a plurality of point linking pairs, each point linking pair comprising a contour point on the endocardial contour and a contour point on the epicardial contour, and the two contour points of each point linking pair being located on the same normal of a reference contour of a left ventricle wall in the reference image slice; a point linking pair tracking section configured to determine locations of each point linking pair in other image slices of the image slice time series; and a motion vector calculation section configured to calculate, according to the locations of the plurality of point linking pairs in adjacent image slices of the image slice time series, a motion vector of the myocardium of the left ventricle between the adjacent image slices, the myocardium being defined by the endocardial contour and the epicardial contour.

In accordance with another aspect of the present invention, there is provided a myocardial motion analysis apparatus for analyzing a motion of a myocardium of a left ventricle in a three-dimensional medical image time series, the three-dimensional medical image time series comprising a plurality of three-dimensional images acquired at a plurality of time points in a cardiac cycle, each of the three-dimensional images consisting of a plurality of parallel two-dimensional image slices that are intersected with a long axis of the left ventricle, and the two-dimensional image slices located at the same location in the three-dimensional images forming an image slice time series. The apparatus comprising: an analysis section implemented by the myocardial motion analysis apparatus according to the above aspect of the present invention, and configured to analyze the motion of the myocardium of the left ventricle in each medical image slice time series. The motions of the myocardium generated in the plurality of two-dimensional image slices at the same time point form a motion of the left ventricle at this time point.

Moreover, according to still another aspect of the present invention, there is provided a computer program for realizing the foregoing methods.

Additionally, according to still a further aspect of the present invention, there is provided a computer program product, which is in the form of at least a computer readable medium, on which computer program codes for realizing the foregoing methods are recorded.

Embodiments of the present invention are described below with reference to the accompanying drawings. The sections and features described in a figure or an embodiment of the present invention can be combined with the sections and features shown in one or more other figures or embodiments. It should be noted that, for the purpose of clarity, representations and descriptions of sections and processes which are known to those skilled in the art or are not related to the present invention, are not presented in the drawings and the description.

Exemplary embodiments of the present invention are described below in the following order:

1. Moving object contour tracking method
2. Moving object contour tracking method for a three-dimensional image time series
3. Myocardial motion analysis method
4. Myocardial motion analysis method for a three-dimensional medical image time series
5. Moving object contour tracking apparatus
6. Moving object contour tracking apparatus for a three-dimensional image time series
7. Myocardial motion analysis apparatus
8. Myocardial motion analysis apparatus for a three-dimensional medical image time series
9. Computer structure capable of implementing the methods/apparatuses disclosed in the embodiments of the preset invention <1. Moving Object Contour Tracking Method>

The moving object contour tracking method according to embodiments of the present invention is described below with reference to FIG. 1-FIG. 12B.

The moving object contour tracking method according to the embodiments of the present invention is configured to track a contour of a moving object which deforms periodically in an image slice time series. An image slice time series includes a plurality of image slices that are respectively acquired for the moving object at a plurality of time points in a motion period of the moving object. It should be appreciated that the moving object contour tracking method provided in the embodiments of the present invention can be used for tracking a contour of a moving object in various types of image slice time series. As an example but not a limitation, the image slice time series can be a medical image series formed by examinee data obtained through a medial diagnostic device. The medial diagnostic device includes but is not limited to an X-ray imaging diagnostic device, an ultrasonic diagnostic imaging device, a computed tomography (CT) device, a magnetic resonance imaging (MRI) diagnostic device and a positron emission tomography (PET) device and the like.

FIG. 1 is a schematic flow chart illustrating a moving object contour tracking method according to an embodiment of the present invention. In this embodiment, a contour of a moving object is tracked respectively in two time directions, and the tracking result with a higher reliability is taken as the contour of the moving object, thus improving the accuracy of the contour tracking.

As shown in FIG. 1, in step S110, contour tracking is performed in an image slice time series in a first time direction to acquire a first contour of the moving object in each image slice. In performing the contour tracking, an initial contour of the moving object in a predetermined image slice of the image slice time series is taken as a starting contour, and the last image slice is taken as the previous image slice of a first image slice in the first time direction. Here, the first time direction may be a time elapsing direction from former to later, or a direction from later to former which is opposite to the time elapsing direction.

As the moving object is deforming periodically and the image slice time series includes the image slices acquired in a motion period of the moving object, the first image slice has a motion correlation with the last image slice, that is, the contours of the moving object in the first and the last image slices are similar. Thus, the last image slice in the first time direction can be taken as the previous image slice of the first image slice without influencing the accuracy of the contour tracking.

It should be appreciated that the predetermined image slice of the image slice time series here may be an image slice a relatively accurate initial contour of which can be acquired easily. The predetermined image slice may be designated manually or be recognized from the image slice time series using an existing technical method based on a predetermined image slice characteristic.

In step S120, the contour tracking is performing in the image slice time series in a second time direction to acquire a second contour of the moving object in each image slice. Similarly, in performing the contour tracking, the initial contour of the moving object in the predetermined image slice is taken as a starting contour. Additionally, the last image slice is taken as the previous image slice of a first image slice in the second time direction. Here, the second time direction, which is a direction opposite to the first time direction, may be a direction from later to former which is opposite to the time elapsing direction, or the time elapsing direction from former to later.

Similarly, as the moving object is deforming periodically and the image slice time series includes the image slices acquired in a motion period of the moving object, taking the last image slice in the second time direction as the previous image slice of the first image slice will not influence the accuracy of the contour tracking.

In step S130, a similarity between the first contour of the moving object in the predetermined image slice and the initial contour of the moving object in the predetermined image slice is calculated as a first similarity, and a similarity between the second contour of the moving object in the predetermined image slice and the initial contour of the moving object in the predetermined image slice is calculated as a second similarity. In both of the first and second time directions, the contour of the moving object in the predetermined image slice acquired through the contour tracking is the contour acquired by the last tracking in the contour tracking. In addition, as stated above, taking the last image slice in the first or second time direction as the previous image slice of the first image slice will not influence the accuracy of the contour tracking.

Therefore, if the similarity between a tracked contour and the initial contour of the moving object in the predetermined image slice is higher, then it may be determined that the contour tracking performed in the respective time direction has a higher accuracy, that is, a higher reliability.

In step S140, the contours in the image slices tracked in the contour tracking direction (the first or second time direction) corresponding to a greater one of the first and second similarities are taken as the contours of the moving object in the respective image slices.

By performing complete contour tracking respectively in the two time directions and comparing the tracked contours with the initial contour, a tracked contour with a higher reliability can be selected as the contour of the moving object, thereby improving the accuracy of the contour tracking.

Figure 2:
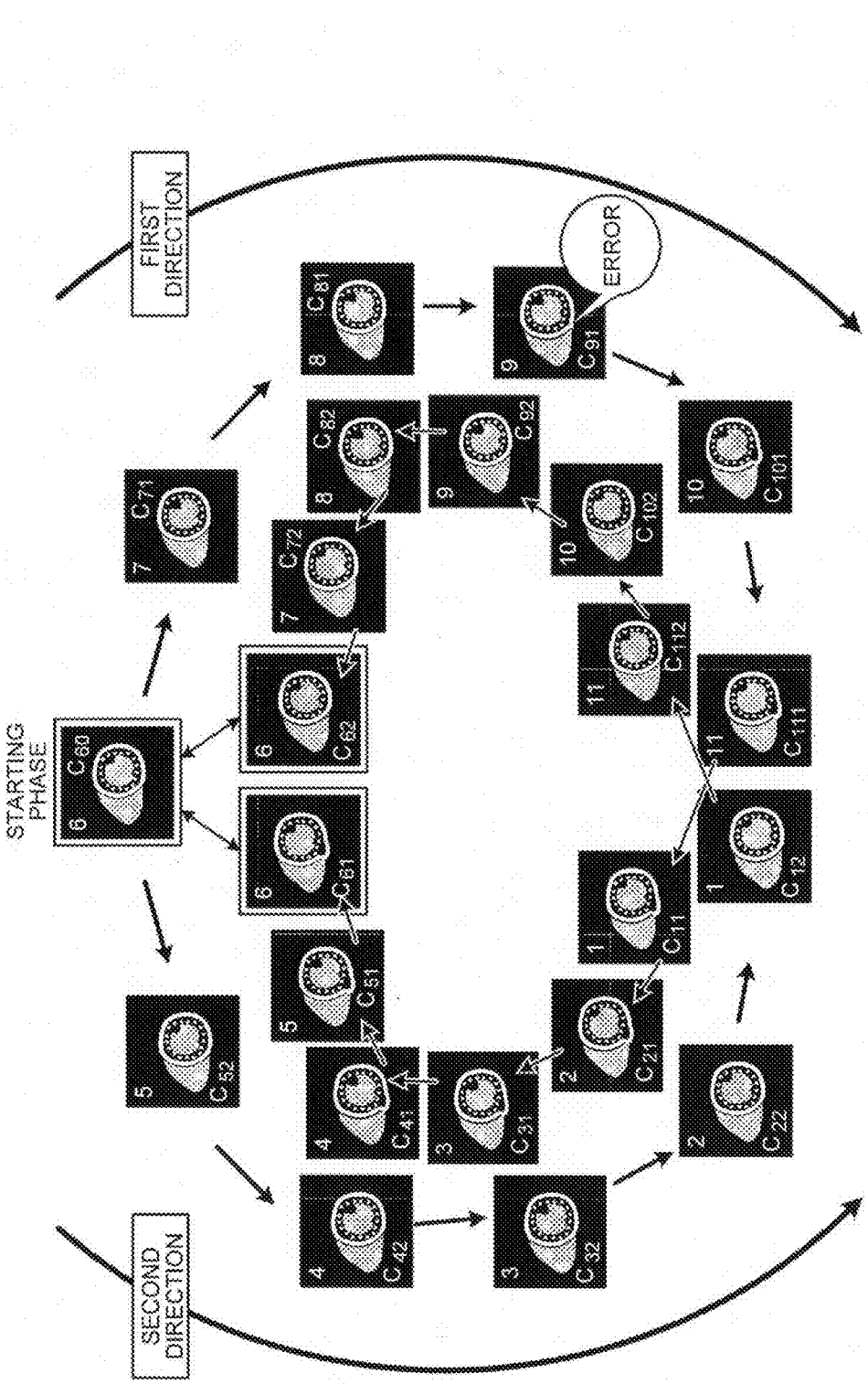
FIG. 2 shows an application example of the moving object contour tracking method according to the embodiment of the present invention.

In order to facilitate understanding, FIG. 2 shows an application example of the moving object contour tracking method according to the embodiment of the present invention. This example shows an image slice time series consisting of a plurality of image slices that are acquired by an MRI device from a section of a left ventricle intersected with a long axis of the left ventricle (that is, the long axis of a heart) at a plurality of time points of a cardiac cycle. The image slice time series includes 11 image slices that are numbered from 1 to 11 in time sequence from former to later. In each image slice, an epicardial contour of the left ventricle is denoted with a solid line, and an endocardial contour of the left ventricle is denoted with a dotted line. Only an epicardial contour tracking process is described herein, and an endocardial contour tracking process is a similar process and therefore is not described repeatedly.

In this example, the image slice 6, which is an image slice in an end-systolic phase, is taken as a predetermined image slice. At the end-systolic phase, the left ventricle presents an obvious edge and a regular shape, which facilitates the contour determination of the left ventricle. The image slice in the end-systolic phase can be designated manually or recognized among the image slice time series using any proper existing method. As an example but not a limitation, the image in the end-systolic phase can be detected from the image slice time series according to area, or determined according to an external signal by comparison with a synchronous electrocardiogram.

By taking an initial epicardial contour of the left ventricle in the image slice 6 as a starting contour to perform contour tracking in the first time direction (as an example, the first time direction in this example is the time elapsing direction) indicated by an arrow shown in FIG. 2, first epicardial contours C71 to C111 and C11 to C61 of the left ventricle in the image slices 7-11 and 1-6 are acquired one by one. In this tracking process, the last image slice 11 in the first time direction is taken as the previous image slice of the first image slice 1.

By taking the initial epicardial contour of the left ventricle in the image slice 6 as a starting contour to perform contour tracking in the second time direction (as an example, the second time direction in this example is a direction opposite to the time elapsing direction) shown by an arrow, second epicardial contours C52 to C12 and C112 to C62 of the left ventricle in the image slices 5-1 and 11-6 are acquired one by one. In this tracking process, the last image slice 1 in the second time direction is taken as the previous image slice of the first image slice 11.

It can be seen that in the tracking process in the first time direction, a tracking error occurs in the epicardial contour in the image slice 9 and is then sequentially propagated to the epicardial contour C61 in the image slice 6. It can be known by calculation that the similarity between the second contour C62 in the image slice 6 serving as the predetermined image slice and the initial contour C60 is higher than the similarity between the first contour C61 and the initial contour C60. Consequently, it can be determined that the contour tracking in the second time direction is more accurate than that in the first time direction. Thus, the epicardial contours acquired in the second time direction can be taken as the epicardial contours of the left ventricle in the respective image slices.

It should be noted that a heart image, which is provided herein as an example for describing the moving object contour tracking method and apparatus, is not to be construed as a limitation to the present invention. To the contrary, the present invention can be applied to any image containing a moving object that deforms periodically.

In order to decrease the amount of calculation, according to another embodiment of the present invention, a first turn of contour tracking is performed at first, and a second turn of contour tracking is performed to correct the result of the first turn of contour tracking only when it is determined according to the result of the first turn of contour tracking that the first turn of contour tracking may have an error. As a specific implementation mode, in an image slice time series including n image slices, by taking an initial contour of the moving object in the sth image slice as a starting contour, a turn of contour tracking is performed respectively in a direction from the (s−1)th to first image slices and a direction from the (s+1)th to the nth image slices to acquire the first contours of the moving object in the (s−1)th to first image slices and in the (s+1)th to nth image slices, wherein s represents the number of the predetermined image slice and 1≤s≤n. The similarity between the first contour of the moving object in the first image slice and the first contour of the moving object in the nth image slice is calculated. If the similarity between the first contour of the moving object in the first image slice and that of the moving object in the nth image slice is lower than a predetermined threshold, indicating that there may be an error in the first turn of contour tracking, a second turn of contour tracking is performed. In the second turn of contour tracking, by taking the first contour of the moving object in the first image slice as a starting contour, the contour tracking is performed in a direction from the nth image slice to the sth image slice to acquire the second contours of the moving object in the nth to (s−1)th image slices and a first contour of the moving object in the sth image slice; and by taking the first contour of the moving object in the nth image slice as a starting contour, the contour tracking is performed in a direction from the first image slice to the sth image slice to acquire the second contours of the moving object in the first to sth image slices. The similarity between the first contour and the initial contour of the moving object in the sth image slice and the similarity between the second contour and the initial contour of the moving object in the sth image slice are respectively calculated. If the similarity between the first contour and the initial contour of the moving object in the sth image slice is greater than that between the second contour and the initial contour of the moving object in the sth image slice, the first contours of the moving object in the (s−1)th to first image slices are taken as the contours of the moving object in the (s−1)th to first image slices, and the contours of the moving object in the nth to (s+1)th image slices are taken as the contours of the moving object in the nth to (s+1)th image slices, vice versa.

For instance, for the image slice time series shown in FIG. 2, the initial contour in the image slice 6 can be taken as a starting contour to track the epicardial contours in the image slices 5-1 in a direction opposite to the time elapsing direction and the epicardial contours in the image slices 7-11 in the time elapsing direction. Here, consuming that the image slice time series shown in FIG. 2 includes a plurality of image slices acquired in one motion period of the left ventricle, image slices 1 and 11 are two adjacent image slices in location in the motion period. The epicardial contours in the image slices 1 and 11 are compared. If the difference between the epicardial contours in image slices 1 and 11 is small, then it is considered that the tracking results acquired in the two directions both are accurate and no second turn of tracking is needed. If the difference between the epicardial contours in image slices 1 and 11 is big, it is considered that there is an error in the tracking in one of the two directions, and then, the contour tracking of epicardial contour is continued in the image slices 1-6 (starting from the image slice 11) in time elapsing direction, and continued in the image slices 11-6 (starting from the image slice 1) in the direction opposite to the time elapsing direction. Then the similarity comparison as described above is carried out to select the result acquired in the tracking direction with a higher similarity as the epicardial contours of the left ventricle.

In addition, according to another embodiment of the present invention, after the similarity comparison is carried out, the contours acquired in the contour tracking direction corresponding to the lower similarity may be corrected with the contours acquired in the contour tracking direction corresponding to the greater similarity so as to acquire final contours. Any proper existing method can be used to perform the correction. As an example but not a limitation, the average of the contours acquired in the two contour tracking directions may be calculated as the final contours.

Additionally, when the image slice time series fails to cover a complete motion period, the first image slice and the last image slice are not so adjacent in the motion period as they are in the case where the image slice time series covers a complete motion period, and consequentially, the similarity between the first image slice and the last image slice may be lower than that in the case where the image slice time series covers a complete motion period. In this situation, the image slices corresponding to the uncovered part of the motion period may be predicted through image interpolation, and then the predicted image slices and the original image slices are used together to perform the contour tracking, so as to eliminate the influence caused by the lower similarity between the first and last image slices and to improve the accuracy of the contour tracking.

Whether the image slice time series covering a complete motion period can be determined using existing methods. For example, it can be determined by comparing the time information carried by each image slice with the motion period information of the moving object that may be externally input. If the time interval spanned by the image slice time series (that is, the time interval between the first and last image slices in the image slice time series) is shorter than the motion period, it is determined that the image slice time series fails to cover the complete motion period.

The one or more image slices corresponding to the uncovered part of the motion period may be predicted using any proper existing image interpolation method, for example, the nearest-neighbor interpolation and the bilinear interpolation. For instance, in the case where the contour tracking is performed in the first time direction, the last image slice in the first time direction is taken as a source image and the first image slice in the first time direction is taken as a target image slice to predict the one or more image slices between the last and first image slices using an image interpolation method; and in the case where the contour tracking is performed in the second time direction, the last image slice in the second time direction is taken as the source image and the first image slice in the second time direction is taken as the target image slice to predict the one or more image slices between the last and first image slices using an image interpolation method.

The number of the image slices to be predicted can be determined according to the ratio of the length of the uncovered part of the motion period to the interval between adjacent image slices of the image slice time series.

Then, tracking is performed in the image slice time series consisting of the original image slices and the predicted image slices is tracked in each time direction.

For instance, for the example shown in FIG. 2, the interval between the image slices 1 and 11 can be compared. If the interval is smaller than the cardiac cycle of the left ventricle, then the image slices to be interpolated between the image slices 1 and 11 are respectively predicted in the first and second time directions using an image interpolation method. Then, an image slice time series including the original image slices 1-11 and the interpolated image slices is tracked in the contour tracking in the two time direction.

In the moving object contour tracking method according to the embodiment of the present invention, the contour tracking step may be realized using any proper existing method without limitation. As an example, FIG. 3 is a schematic flow chart illustrating a contour tracking step according to an embodiment of the present invention.

Figure 3:
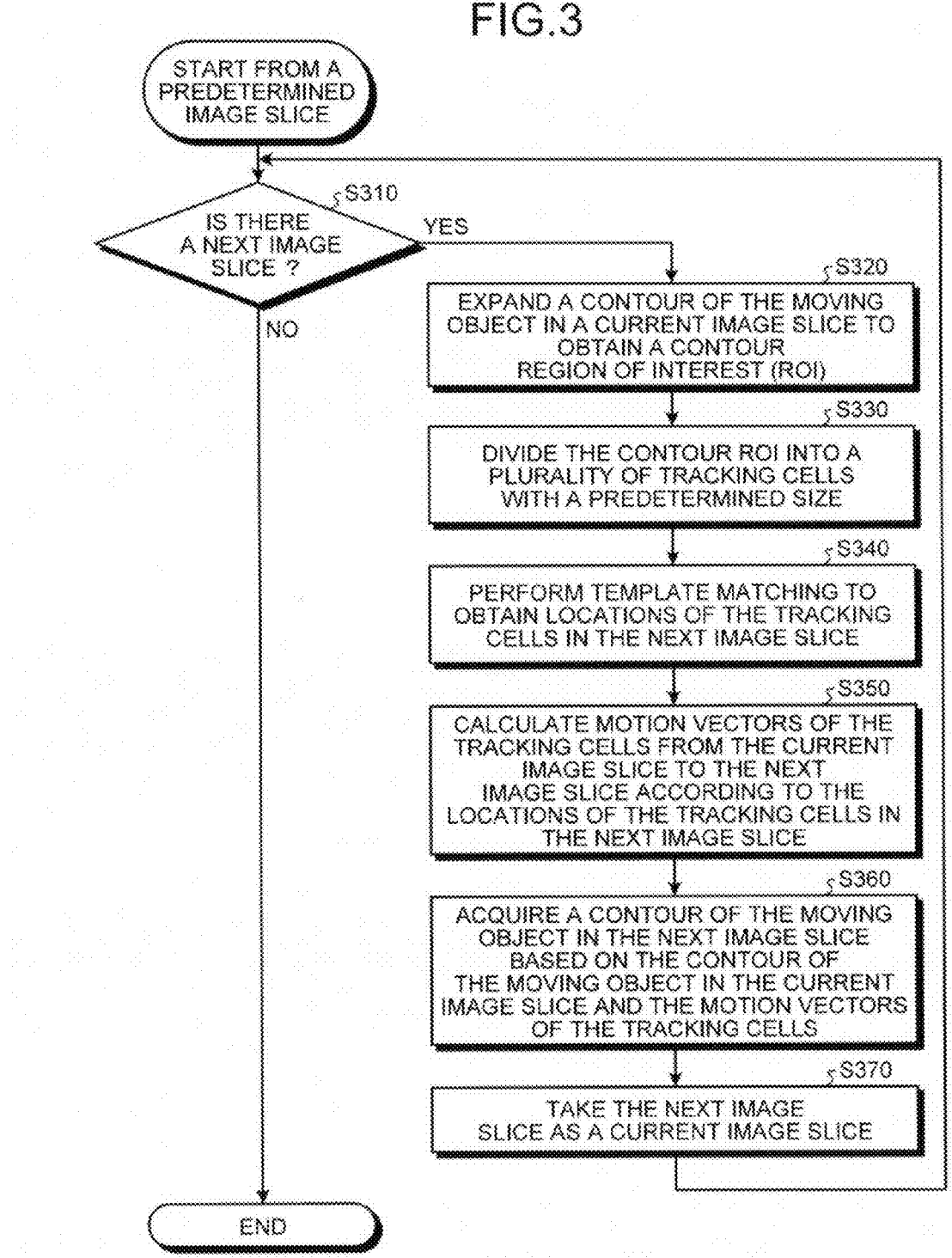
FIG. 3 is a schematic flow chart illustrating a contour tracking step according to an embodiment of the present invention.

As shown in FIG. 3, starting from a predetermined image slice, if it is determined in step S310 that there exists a next image slice of the image slice time series, the process proceeds to perform the contour tracking from step S320 to step S360; and otherwise, the process is ended.

In step S320, the contour of the moving object in the current image slice is expanded to obtain a contour region of interest (ROI). For instance, the contour of the moving object can be expanded with a predetermined width to obtain the contour ROI.

In step S330, the contour ROI is divided into a plurality of tracking cells with a predetermined size.

Figure 4:
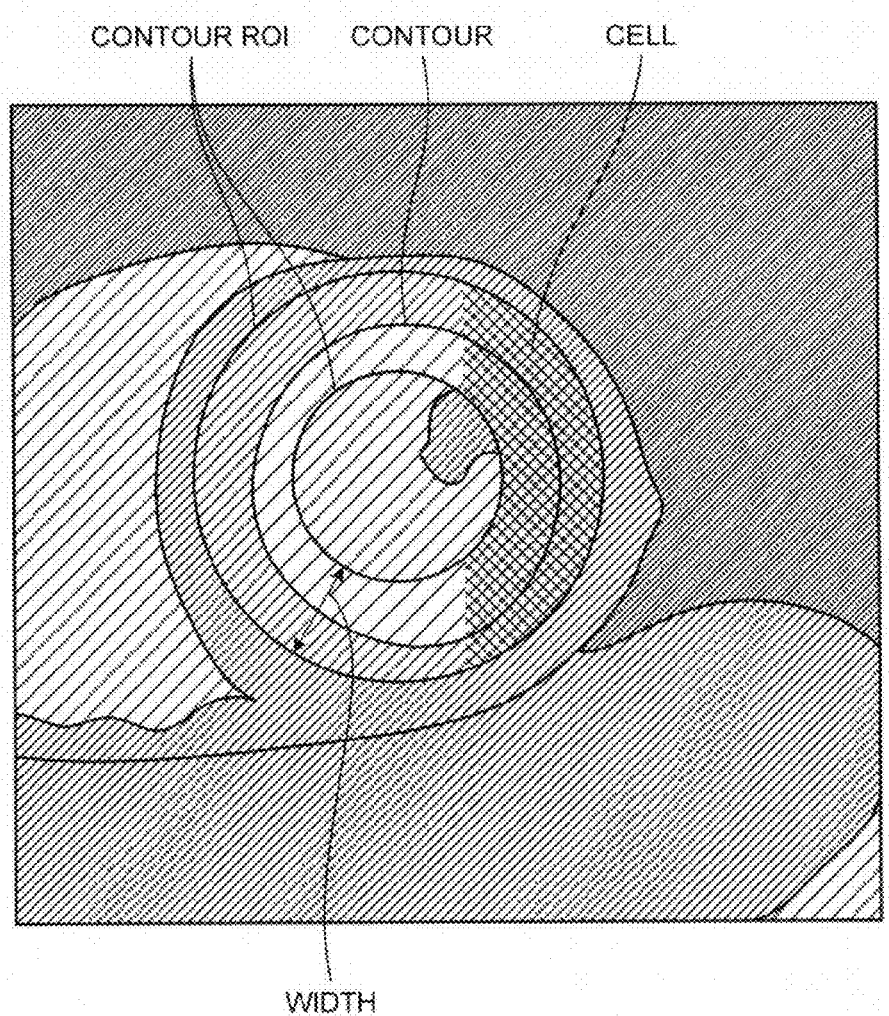
FIG. 4 shows examples of a contour region of interest (ROI) and a tracking cell.

In order to facilitate understanding, FIG. 4 shows an example of a contour ROI and tracking cells.

In step S340, locations of the plurality of tracking cells in the next image slice is obtained by template matching. Here, the template matching for the tracking cells can be carried out using any proper existing template matching method, which will not be described in detail herein.

In step S350, the motion vectors of the plurality of tracking cells from the current image slice to the next image slice are calculated according to the locations of the plurality of tracking cells in the next image slice. For instance, the average location of the pixels in a tracking cell or the location of the central pixel of the tracking cell can be taken as the location of the tracking cell.

In step S360, the contour of the moving object in the next image slice is acquired based on the contour of the moving object in the current image slice and the motion vectors of the plurality of tracking cells from the current image slice to the next image slice.

As a specific implementation mode, a weighted average of the motion vectors of tracking cells within a predetermined range and adjacent to each contour point on the contour of the moving object in the current image slice can be calculated as a motion vector of the contour point from the current image slice to the next image slice. Then, the contour of the moving object in the current image slice is moved according to the motion vector of each contour point on the contour of the moving object in the current image slice to acquire the contour of the moving object in the next image slice.

In the exemplary embodiments described above, the examples are explained in which contour tracking is performed in a plurality of image slices acquired at a plurality of time points in a motion period of the moving object. However, the embodiments are not limited to these examples. For example, contour tracking is performed in a plurality of image slices acquired at a plurality of time points in a predetermined period of the moving object. For example, among the image slices 1-11 shown in FIG. 2, first epicardial contours C41 to C61 of the left ventricle in the image slices 4-6 are acquired one by one. second epicardial contours C82 to C62 of the left ventricle in the image slices 8-6 are acquired one by one. Then the similarity comparison as described above is carried out to select the result acquired in the tracking direction with a higher similarity as the epicardial contours of the left ventricle.

In the moving object contour tracking method according to an embodiment of the present invention, the initial contour of the moving object in the predetermined image slice is acquired in advance. The initial contour of the moving object can be acquired using any existing method, or can be depicted manually. As an example, a method for acquiring the initial contour of the moving object according to an embodiment of the present invention is described below.

In the following embodiment, the moving object is a left ventricle, the image slice time series includes a plurality of image slices that are acquired with respect to a section of the left ventricle intersected with the long axis of the left ventricle at a plurality of time points in a cardiac cycle. The left ventricle has an endocardial contour and an epicardial contour, and a method for acquiring an initial endocardial contour and a method for acquiring an initial epicardial contour are respectively described below.

In the following embodiment, considering that the contours of the endocardium and the epicardium of the left ventricle are both curves, the contour of the endocardium tends to be influenced by a papillary muscle, and the contour of the epicardium is relatively blurry, the original image slices are converted to a polar coordinate system so that the contours of the endocardium and the epicardium can be extracted from the image slices more accurately.

Figure 5:
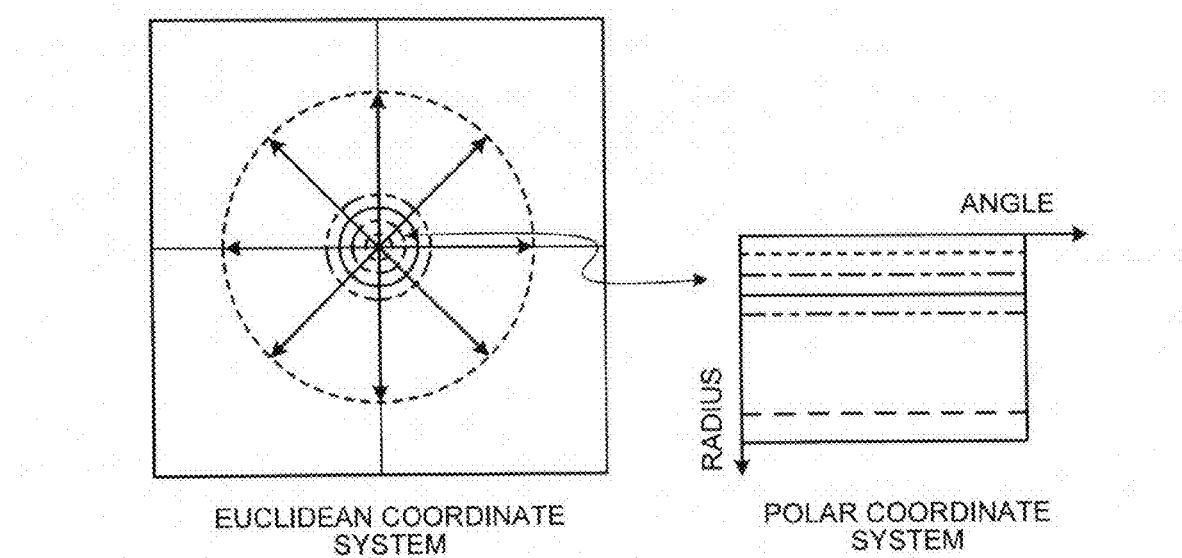
FIG. 5 is a schematic diagram illustrating a conversion relationship between a Euclidean coordinate system and a polar coordinate system.

In order to facilitate understanding, FIG. 5 shows a schematic diagram illustrating a conversion relationship between a Euclidean coordinate system and a polar coordinate system. In this figure, the origin of the Euclidean coordinate system corresponds to the pole of the polar coordinate system. The horizontal coordinate in the polar coordinate system represents the angle of a line between a point in the Euclidean coordinate system and the origin with respect to the positive direction of the horizontal direction of the Euclidean coordinate system, and the vertical coordinate in the polar coordinate system represents a distance between the origin and a point in the Euclidean coordinate system. After being converted to the polar coordinate system, the circles with different radiuses in the Euclidean coordinate system are presented as straight lines with different heights. On the other hand, after being converted into the Euclidean coordinate system, the straight lines with different heights in the polar coordinate system are presented as circles with different radiuses.

FIG. 6 is a schematic flow chart illustrating a method for acquiring an initial contour of a left ventricle according to an embodiment of the present invention. In this embodiment, an endocardial contour of the left ventricle is acquired as the initial contour of the left ventricle.

As shown in FIG. 6, in step S610, a predetermined image slice is converted to the polar coordinate system. Here, as an example, the predetermined image slice may be an image slice in an end-systolic phase. In actual applications, in order to decrease the amount of calculation, only the motion area part in the predetermined image slice, rather than the whole image slice, may be converted to the polar coordinate system.

In step S620, the endocardial contour of the left ventricle is acquired in the polar coordinate system as the initial contour of the left ventricle in the predetermined image slice. In the polar coordinate system, the contour of the endocardium is approximate to a straight line. In addition, in the polar coordinate system, various kinds of information projected in the horizontal direction (the direction of the horizontal axis) such as brightness (typically represented with a pixel value) and edge can be used, which will be described later.

In step S630, the initial contour of the left ventricle acquired in the polar coordinate system is mapped to the original predetermined image slice. In the left ventricle, the endocardial contour line obtained by a common method may be relatively small due to the influence of the papillary muscle. Therefore, in the acquisition of the endocardial contour of the left ventricle, it is an important task to eliminate the influence of the papillary muscle and to contain the papillary muscle in a range defined by the contour line of the endocardium so as to obtain a bigger and more accurate endocardial contour.

The endocardial contour of the left ventricle in the predetermined image slice can be acquired in the polar coordinate system using any proper existing method. As an example, FIG. 7 shows a schematic flow chart illustrating acquisition of an endocardial contour of a left ventricle according to an embodiment of the present invention. In this embodiment, a rough location of the endocardial contour is determined in the polar coordinate system using a horizontal projection of an image slice, and then the endocardial contour is acquired from the edge image of the image slice using a straight line detection method.

As shown in FIG. 7, in step S710, edges are detected in the predetermined image slice to acquire an edge image of the predetermined image slice.

In step S720, a radius of the endocardial contour of the left ventricle in the predetermined image slice is acquired in the polar coordinate system using the horizontal projection of a gray scale image of the predetermined image slice. It can be seen from the original image slice of the left ventricle shown in FIG. 2 that the gray scale of the myocardium of the left ventricle is smaller than the part inside the left ventricle. Accordingly, the location where a pixel value drops sharply in the horizontal projection of the gray scale image of the image slice can be taken as the location of the radius of the endocardial contour.

Then, in step S730, the endocardial contour of the left ventricle is acquired in the polar coordinate system from the edges nearby the radius of the endocardial contour of the left ventricle using a straight line detection method.

Figure 8A:
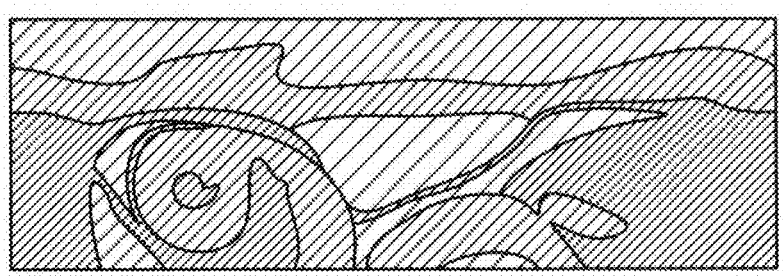
FIG. 8A shows an example of a gray scale image of an image slice in a polar coordinate system.
Figure 8B:
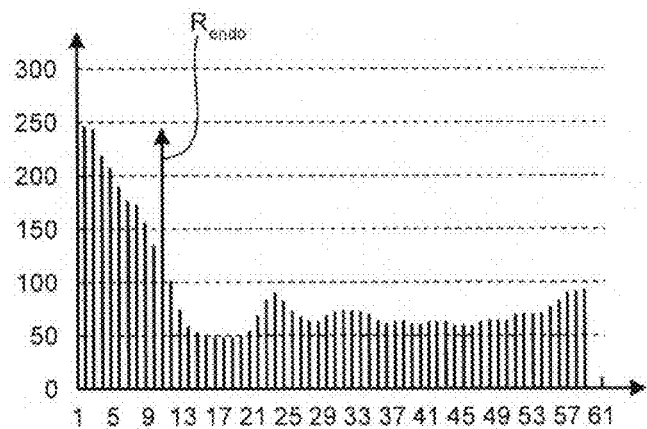
FIG. 8B shows an example of a horizontal projection of the gray scale image shown in FIG. 8A.

In order to facilitate understanding, FIG. 8A shows an example of a gray scale image of a predetermined image slice in a polar coordinate system, and FIG. 8B shows an example of a horizontal projection the gray scale image shown in FIG. 8A. In FIG. 8B, the horizontal coordinate represents a row in the gray scale image of the image slice, and the vertical coordinate represents the sum or average of the pixel values in a row. An image slice is divided into rows by taking one or more pixels as a unit, depending on different demands on accuracy. As shown in FIG. 8B, the location where the sum or average of pixel values drops sharply is determined as the location of the radius Rendo of the endocardial contour.

In the foregoing embodiment, the straight line detection method may be a Hough transformation method. In Comparison with other straight line detection methods, which take into consideration an edge pixel with a small radius and therefore tends to be influenced by the papillary muscle, the Hough transformation method, when used for fitting edge pixels (also referred to as edge points), can acquire a contour containing the majority of edge points and eliminate the influence caused by edge points such as the papillary muscle and noise.

FIG. 9 is a schematic flow chart illustrating acquisition of an initial contour of a left ventricle according to another embodiment of the present invention. In this embodiment, the epicardial contour of the left ventricle is acquired as the initial contour of the left ventricle.

As shown in FIG. 9, in step S910, a predetermined image slice is converted to a polar coordinate system. Similarly, as an example, the predetermined image slice may be an image slice in an end-systolic phase. In actual applications, in order to decrease the amount of calculation, only a motion area part in the predetermined image slice rather than the whole image slice may be converted to the polar coordinate system. In step S920, the epicardial contour of the left ventricle is acquired in the polar coordinate system as the initial contour of the left ventricle in the predetermined image slice. In step S930, the initial contour of the left ventricle acquired in the polar coordinate system is mapped to the original predetermined image slice.

The epicardial contour of the left ventricle in the predetermined image slice can be acquired in the polar coordinate system using any proper existing method. As an example, FIG. 10 is a schematic flow chart illustrating acquisition of an epicardial contour of a left ventricle according to an embodiment of the present invention. In this embodiment, edge pixels of an endocardial contour and a thickness of a myocardium are determined using the horizontal projection of an image slice to determine a rough location of the epicardial contour in the polar coordinate system, and then the epicardial contour can be acquired from an edge image of the image slice using a curve fitting method.

As shown in FIG. 10, in step S1010, edges in the predetermined image slice are detected to acquire an edge image of the predetermined image slice.

In step S1020, a radius of the endocardial contour of the left ventricle in the predetermined image slice is acquired in the polar coordinate system using the horizontal projection of a gray scale image of the predetermined image slice.

In step S1030, the thickness of the myocardium of the left ventricle is determined in the polar coordinate system using a horizontal projection of an edge image of the predetermined image slice and the radius of the endocardial contour, thereby acquiring a radius of the epicardium of the left ventricle in the predetermine image slice.

In step S1040, the epicardial contour of the left ventricle is acquired from the edges nearby the radius of the epicardial contour of the left ventricle in the polar coordinate system using any curve fitting method such as a least square method.

Figure 11A:
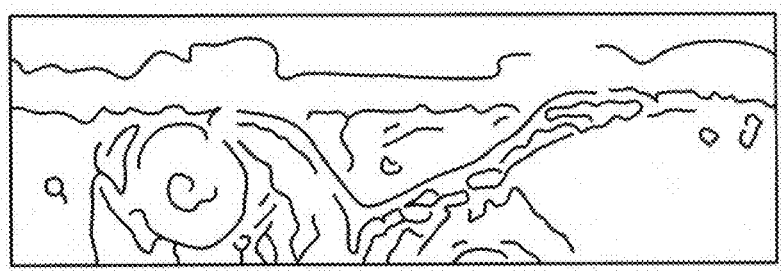
FIG. 11A shows an example of an edge image of an image slice in a polar coordinate system.
Figure 11B:
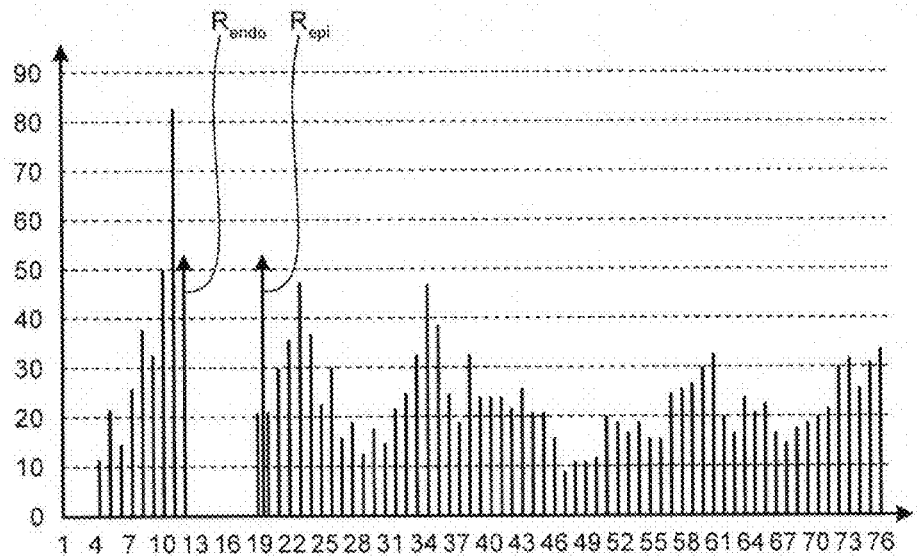
FIG. 11B shows an example of a horizontal projection of the edge image shown in FIG. 11A.

In order to facilitate understanding, FIG. 11A shows an example of an edge image of a predetermined image slice in a polar coordinate system, and FIG. 11B shows an example of a horizontal projection of the edge image shown in FIG. 11A. In FIG. 11B, the horizontal coordinate represents a row in the edge image of the image slice, and the vertical coordinate represents the sum or average of the pixel values in a row. The predetermined image slice is divided into rows by taking one or more pixels as a unit, depending on different demands on accuracy. As shown in FIG. 11B, a location where the sum or average of pixel values drops sharply is determined as the location of the radius Rendo of the endocardial contour. In the edge image, as the myocardium part between the endocardial contour and the epicardial contour substantially contains no edge, there is a gap between the endocardial contour and the epicardial contour in the horizontal projection. Thus, as shown in FIG. 11B, the gap immediately next to the location of the radius Rendo of the endocardial contour is determined as a thickness of the myocardium between the endocardial contour and the epicardial contour, and the location behind the gap is the location of the radius Repi of the epicardial contour.

Figure 12A:
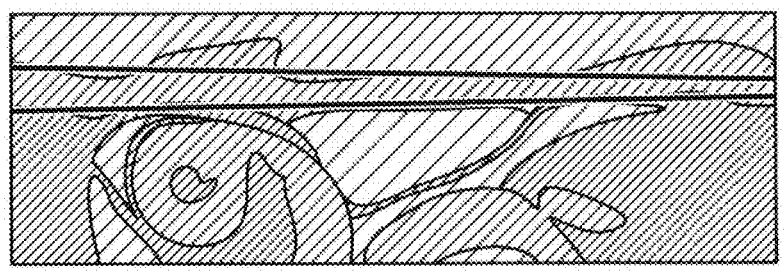
FIG. 12A shows examples of an endocardial contour and an epicardial contour acquired in a polar coordinate system.
Figure 12B:
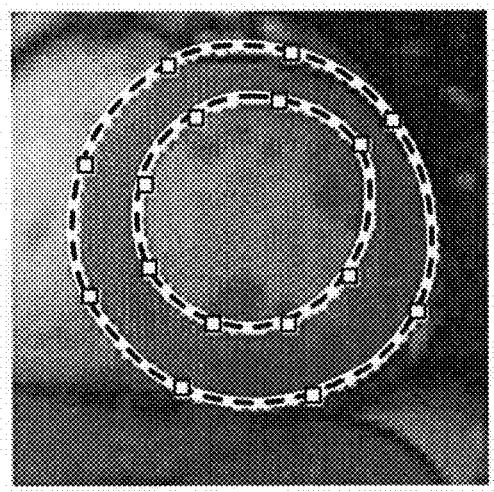
FIG. 12B shows an example of conversion of the endocardial contour and the epicardial contour acquired in FIG. 12A into an original image slice.

In order to facilitate understanding, FIG. 12A shows examples of an endocardial contour and an epicardial contour acquired in a polar coordinate system according to the foregoing embodiment. In FIG. 12A, the upper contour line represents an endocardial contour, and the lower contour line represents an epicardial contour. FIG. 12B shows an example of conversion of the endocardial contour and the epicardial contour acquired in FIG. 12A to an original image slice. The endocardial contour shown in FIG. 12B is relatively smooth and includes no protrusion, that is, the influence of the papillary muscle is eliminated.

<2. Moving Object Contour Tracking Method for a Three-Dimensional Image Time Series>

Figure 13:
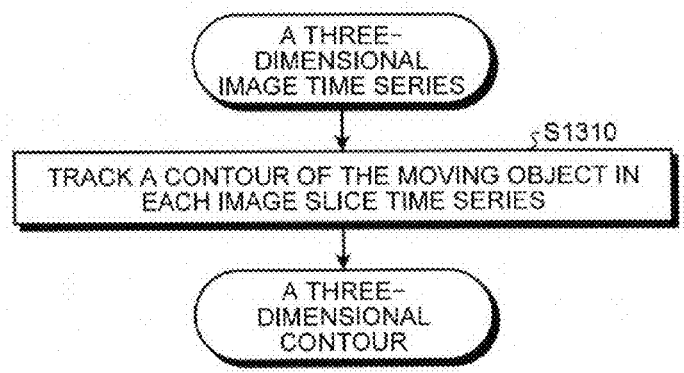
FIG. 13 is a schematic flow chart illustrating a moving object contour tracking method according to another embodiment of the present invention.

FIG. 13 is a schematic flow chart illustrating a moving object contour tracking method according to another embodiment of the present invention.

The moving object contour tracking method provided according to this embodiment is used to track the contour of a periodically deforming object in a three-dimensional image time series. The three-dimensional image time series includes a plurality of three-dimensional images that are acquired at a plurality of time points in a motion period of the moving object. Each of the three-dimensional images consists of a plurality of parallel two-dimensional image slices. The two-dimensional image slices located at the same location in the three-dimensional images form an image slice time series.

As shown in FIG. 13, in this method, in step S1310, the contour of the moving object is respectively tracked in each image slice time series. Here, the contour of the moving object is tracked in each image slice time series using the moving object contour tracking method described in the part <1. Moving object contour tracking method>. The contours of the moving object in the plurality of two-dimensional image slices at the same time point form a three-dimensional contour of the moving object at this time point.

In a three-dimensional image time series, there may be some image slice time series which are beyond the real range of the moving object. The contours of the moving object tracked in these image slice time series are unreal and, if being adopted, will undermine the accuracy of the subsequent calculation of some parameters of the moving object. On this ground, in an embodiment of the present invention, before the contour tracking of the moving object, such undesired image slice time series as described above are determined, and are not subjected to the contour tracking or are directly deleted to avoid the influence on the accuracy of the subsequent parameter calculation.

For a three-dimensional image time series acquired by an MRI device in a short axis direction of a heart, when the left ventricle is taken as a moving object, the two image slice time series corresponding to the two ends of the moving object are respectively the image slice time series at a base part and that at an apex part.

The image slice time series corresponding to the two ends of the moving object may be recognized using any proper existing method that will not be described herein in detail.

<3. Myocardial Motion Analysis Method>

A myocardial motion analysis method according to embodiments of the present invention is described below with reference to FIG. 14-FIG. 18. The myocardial motion analysis method according to the embodiments of the present invention is used for analyzing the motion of a myocardium of a left ventricle in a medical image slice time series. A medical image slice time series includes a plurality of image slices that are acquired with respect to a section of the left ventricle intersected with the long axis of the left ventricle at a plurality of time points in a cardiac cycle.

The motion of the myocardium can be deemed as the motion of endocardial contour points or epicardial contour points. The motion of each contour point can influence the motion of a neighboring contour point. Therefore, the motion of an epicardial contour point can influence that of a corresponding endocardial contour point, and vice versa. In the myocardial motion analysis method according to the embodiments of the present invention, a point linking pair is configured based on the motion correlation of an epicardial contour point and an endocardial contour point, and the motion of the myocardium is represented with the motion of the point linking pair.

Figure 14:
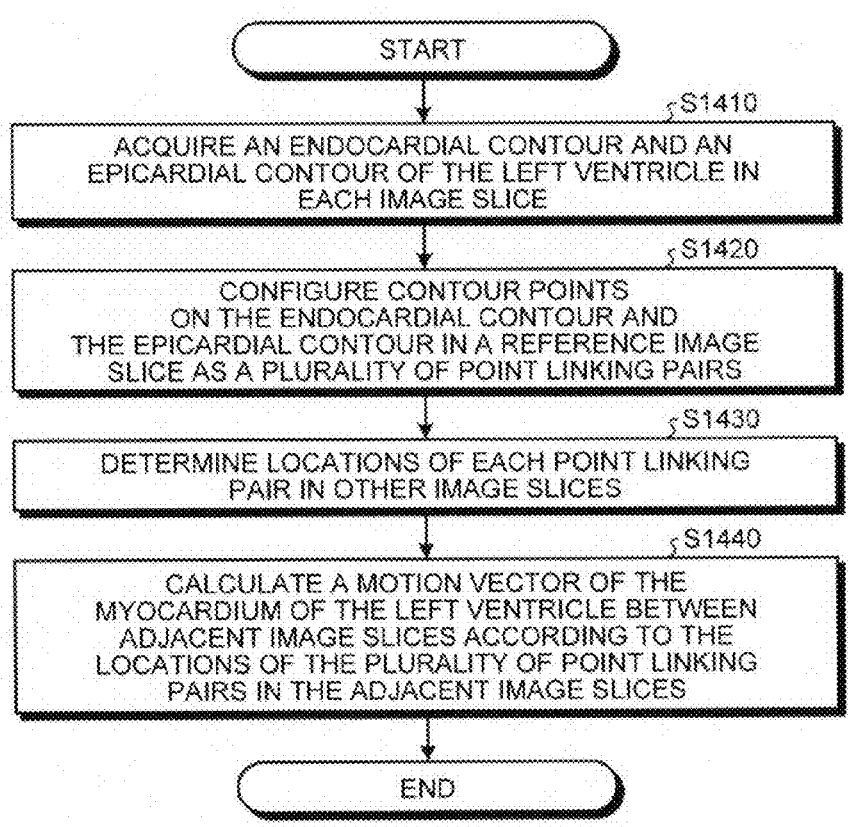
FIG. 14 is a schematic flow chart illustrating a myocardial motion analysis method according to an embodiment of the present invention.

FIG. 14 is a schematic flow chart illustrating a myocardial motion analysis method according to an embodiment of the present invention. As shown in FIG. 14, in step S1410, an endocardial contour and an epicardial contour of a left ventricle are acquired in each image slice. The endocardial contour and the epicardial contour can be marked in each image slice manually or be acquired using any proper existing method. As an example, the endocardial contour and the epicardial contour of the left ventricle can be acquired using the moving object contour tracking method described in the part <1. Moving object contour tracking method> by taking the left ventricle as a moving object.

In step S1420, the contour points on the endocardial contour and the epicardial contour in a reference image slice of the image slice time series are configured as a plurality of point linking pairs, each point linking pair including a contour point on the endocardial contour and a contour point on the epicardial contour that are located on the same normal of a reference contour of a left ventricle wall in the reference image slice. As an example, the reference contour may be the endocardial contour, the epicardial contour or a mean contour acquired from the endocardial contour and the epicardial contour. That is, the line segment defined by each point linking pair is located in a systolic/diastolic direction.

Figure 15:
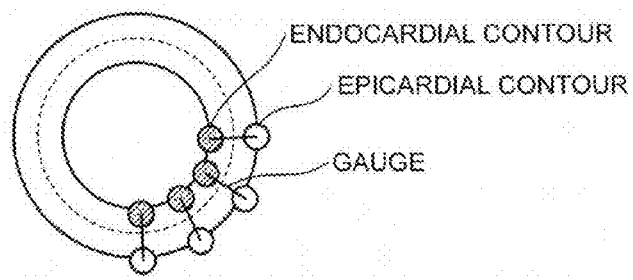
FIG. 15 shows an example of a point linking pair according to the embodiment of the present invention.

In order to facilitate understanding, FIG. 15 shows an example of a point linking pair according to this embodiment. In order to facilitate description, a line segment defined by a point linking pair is referred to as a gauge.

In step S1430, the locations of each point linking pair in other image slices of the image slice time series than the reference image slice are determined.

In step S1440, a motion vector of a myocardium of the left ventricle between adjacent image slices of the image slice time series is calculated according to the locations of the plurality of point linking pairs in the adjacent image slices, wherein the myocardium is defined by the endocardial contour and the epicardial contour of the left ventricle.

Compared with existing myocardial motion analysis methods using separated contour points, the myocardial motion analysis method according to the embodiment of the present invention adds constraints by representing the motion of the myocardium with the motion of the point linking pairs, and therefore can analyze the motion of the myocardium more stably.

In order to analyze the motion of the myocardium comprehensively, according to an embodiment of the present invention, a motion vector of a myocardium between adjacent image slices is resolved into the following motion components: systole/diastole, circumferential expansion/contraction of the myocardium of the left ventricle, rotation of the myocardium of the left ventricle, and twist of the myocardium of the left ventricle.

Figure 16:
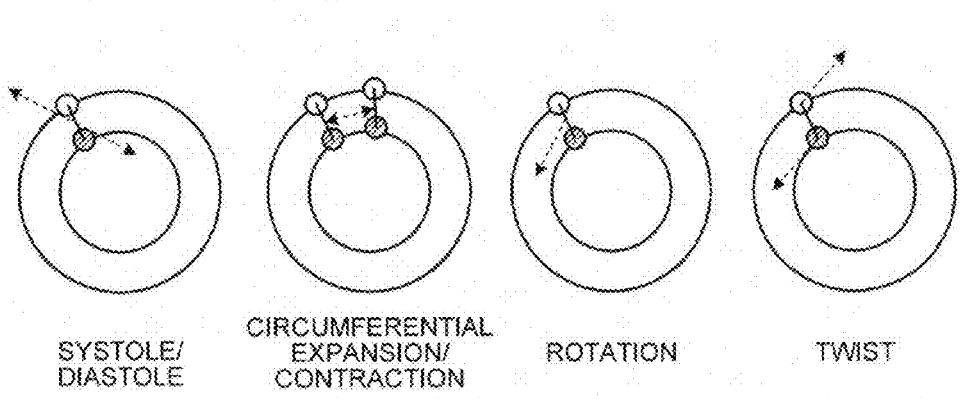
FIG. 16 is a schematic diagram illustrating a myocardial motion component according to an embodiment of the present invention.

In order to facilitate understanding, FIG. 16 is a schematic diagram illustrating a myocardial motion component according to an embodiment of the present invention. In the case where the motion of a myocardium is represented with the motion of point linking pairs, the motion component of systole/diastole can be represented with a component of the variation of the length of a line segment (gauge) defined by a point linking pair in a systole/diastole direction; the circumferential expansion/contraction of the myocardium can be represented by a component of the variation of the distance between two adjacent gauges in the circumferential direction of the reference contour of the left ventricle; the rotation of the myocardium can be represented by a component of the movement (represented with an angle) of a gauge in the circumferential direction of the reference contour of the left ventricle; and the twist of the myocardium can be represented by a component of the difference of the movements (each represented with an angle) of two contour points in a point linking pair in the circumferential direction of the reference contour of the left ventricle.

Under the guide of the foregoing description, those skilled in the art can calculate the respective motion components of the myocardium in any way. A motion component calculation method according to an embodiment of the present invention is described below.

As an example, the motion component of systole/diastole may be calculated by calculating a difference of the projections of a line segment defined by each point linking pair between adjacent image slices, wherein the projections of the line segment are in a normal direction of the reference contour in the reference image slice and the normal direction passes through either of the contour points of the point linking pair.

As an example, the motion component of circumferential expansion/contraction of the myocardium of the left ventricle may be calculated by calculating a difference of projections of a distance of a line segment defined by a point linking pair to a line segment defined by an adjacent point linking pair between adjacent image slices, wherein the projections of the distance are in a tangent direction of the reference contour in the reference image slice and the tangent direction passes through the line segment defined by the point linking pair. As an example but not a limitation, the distance may be a distance between the middle point of the line segment defined by the point linking pair and the middle point of the line segment defined by the adjacent point linking pair, or a length of a perpendicular line from either contour point of the point linking pair to the line segment defined by the adjacent point linking pair.

As an example, the motion component of rotation of the myocardium of the left ventricle may be calculated by calculating a difference of angles of a line segment defined by a point linking pair with respect to a normal direction of the reference contour in the reference image slice between adjacent image slices, wherein the normal direction passes through the line segment defined by the point linking pair. As an example but not a limitation, the angle may be an angle of the line segment defined by the point linking pair with respect to a normal of the reference contour in the reference image slice passing through either contour point of the point linking pair or passing through the middle point of the line segment defined by the point linking pair.

As another example, the image slice time series may be converted to a polar coordinate system by taking the center of the reference contour as a pole. The rotation of the myocardium between adjacent image slices may be calculated using variation in an angle, which is presented in the polar coordinate system, of the middle point of a line segment defined by each point linking pair or of either contour point of each point linking pair between adjacent image slices.

As an example, the motion component of twist of the myocardium of the left ventricle may be calculated by calculating a difference of angles of a normal direction of the reference contour in the reference image slice passing through either contour point of each point linking pair and a normal direction of the reference contour in the reference image slice passing through a middle point of a line segment defined by the point linking pair between adjacent image slices.

As another example, the image slice time series may be converted to a polar coordinate system by taking the center of the reference contour as a pole. The twist of the myocardium between adjacent image slices may be calculated according to a variation in an angle difference between adjacent image slices, wherein the angle difference is a difference between an angle of either contour point in each point linking pair in the polar coordinate system and an angle of the middle point of a line segment defined by the point linking pair in the polar coordinate system.

It should be appreciated that the locations of each point linking pair in other image slices in the image slice time series than the predetermined image slice can be determined using any proper existing method. As an example, a method for determining the locations of each point linking pair in the other image slices in the image slice time series according to an embodiment of the present invention is described below.

While acquiring a contour of the moving object, the moving object contour tracking method according to the above embodiments also obtain continuous motion information of contour points of the moving object. In one of the above embodiment, it is described that a weighted average of the motion vectors of tracking cells within a predetermined range and adjacent to each contour point of the contour of the moving object in the current image slice can be calculated as a motion vector of the contour point from the current image slice to the next image slice. Therefore, in an embodiment of the present invention, the location of each contour point in the next image slice may be determined using the motion vectors of the two contour points of a point linking pair from the current image slice to the next image slice, so as to determine the location of the point linking pair in the next image slice.

Specifically, the motion vector of a contour point on the endocardial contour of the left ventricle in the current image slice from the current image slice to the next image slice is calculated using the moving object contour tracking method according to the above embodiments, the left ventricle serving as a moving object; the location of each endocardial contour point in the next image slice is acquired based on the motion vector of the endocardial contour point from the current image slice to the next image slice; the motion vector of a contour point on the epicardial contour of the left ventricle in the current image slice from the current image slice to the next image slice is calculated using the moving object contour tracking method according to the above embodiments, the left ventricle serving as a moving object; the location of each epicardial contour point in the next image slice is acquired based on the motion vector of the epicardial contour point from the current image slice to the next image slice; and the location of each point linking pair in the next image slice is determined based on the locations of each endocardial contour point and each epicardial contour point in the next image slice.

In addition, as a heart is a moving entirety, the motion of the myocardium of the heart should be smooth. In an embodiment of the present invention, the respective motion components of the myocardium are smoothed to provide a more accurate motion vector consisting of the motion components of the myocardium, and consequentially, a more accurate myocardial motion analysis is provided.

Figure 17:
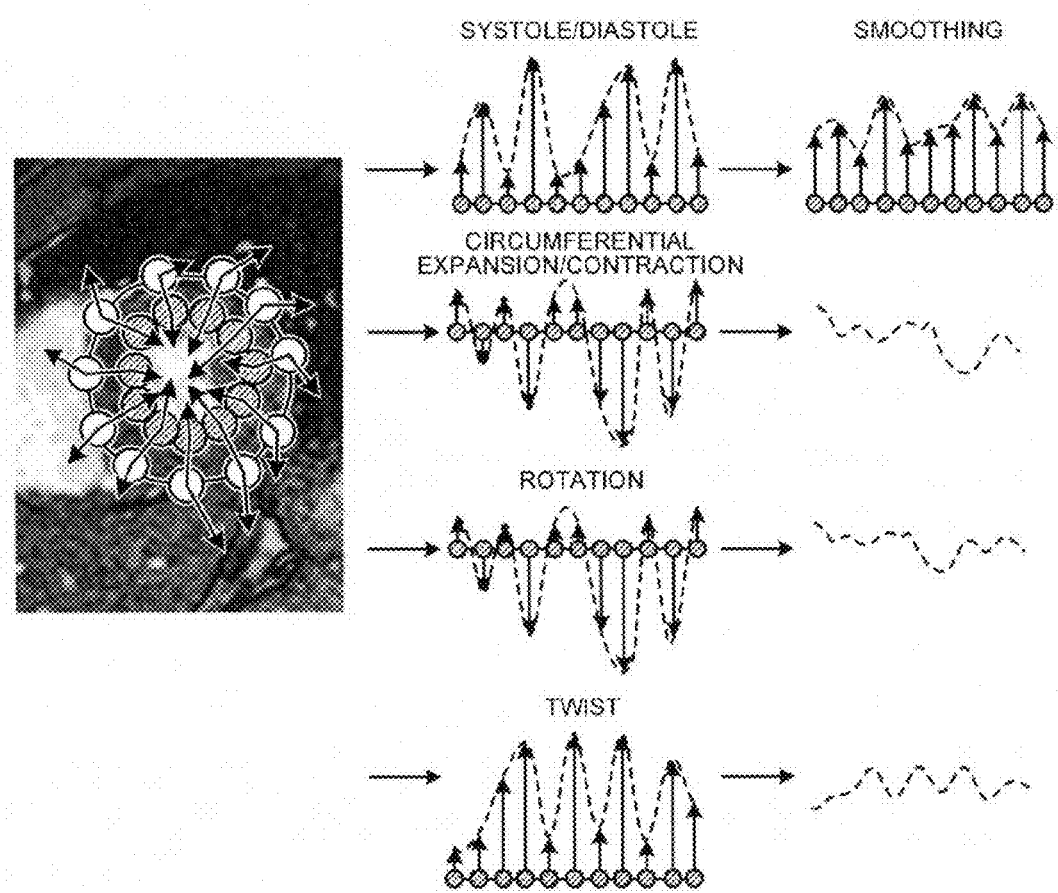
FIG. 17 is a schematic diagram illustrating the smoothing of a motion component time series according to an embodiment of the present invention.

FIG. 17 is a schematic diagram illustrating the smoothing of a motion component time series according to an embodiment of the present invention. As shown in FIG. 17, motion component time series, which are constructed by the respective motion components of the motion vector of the myocardium of a left ventricle between adjacent image slices, are smoothed. As an example but not a limitation, each motion component time series may be smoothed using a Fourier fitting method.

Accordingly, based on the endocardial contour and the epicardial contour of the left ventricle in the reference image slice, a new endocardial contour and a new epicardial contour of the left ventricle in each other image slice of the image slice time series may be acquired by using the smoothed motion component time series of the myocardium of the left ventricle between adjacent image slices, thereby providing a more accurate endocardial contour and epicardial contour.

In physics, strain refers to a relative deformation of an object under an external force. Myocardial strain means the deformation of a myocardium in a cardiac cycle, and can be used to evaluate the regional myocardial systolic and diastolic function and blood supply capability and the myocardial viability. After the motion vector of the myocardium of the left ventricle is acquired using the myocardial motion analysis method provided in the embodiments of the present invention, parameters of the myocardium of the left ventricle such as the myocardial strain, strain force and strain rate may be calculated according to the motion vector of the myocardium between adjacent image slices. There have been a number of existing methods for calculating the parameters such as myocardial strain, strain force and strain rate according to the motion vector of the myocardium and these methods will not be described here in detail.

Figure 18:
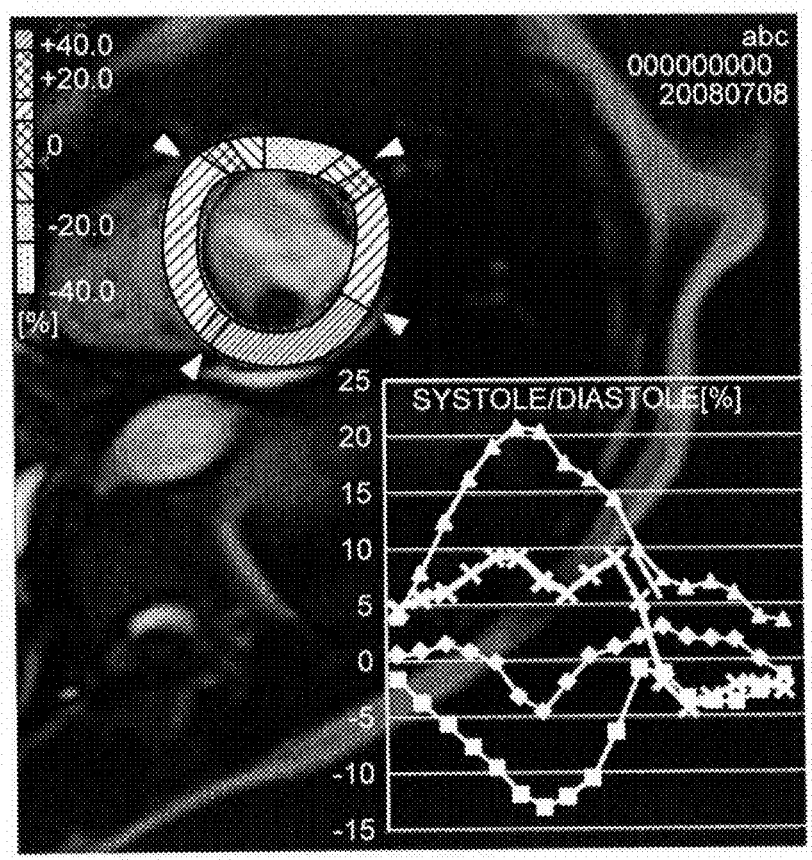
FIG. 18 shows a view of myocardial strains according to an embodiment of the present invention.

In order to present the strains of a myocardium intuitively, the myocardial motion analysis method according to an embodiment of the present invention further includes presenting the strains of the myocardium of the left ventricle on an image. FIG. 18 shows a view of myocardial strains according to an embodiment of the present invention. In this embodiment, there is a color bar at the left-upper side of the view. The different colors in the color bar correspond to different myocardial strains. According to this correspondence relationship, the colors corresponding to the strains of different parts of the myocardium can be overlapped on the respective parts of the myocardium in an image slice so that the doctor can see the strains of the myocardium intuitively. In addition, a curve which shows the strain forces of a myocardium in the systole/diastole directions in a cardiac cycle is shown at the right-lower corner of the view. Under the guide of the foregoing description, those skilled in the art can devise more myocardial strain presentation methods that will not be enumerated herein.

<4. Myocardial Motion Analysis Method for a Three-Dimensional Image Time Series>

Figure 19:
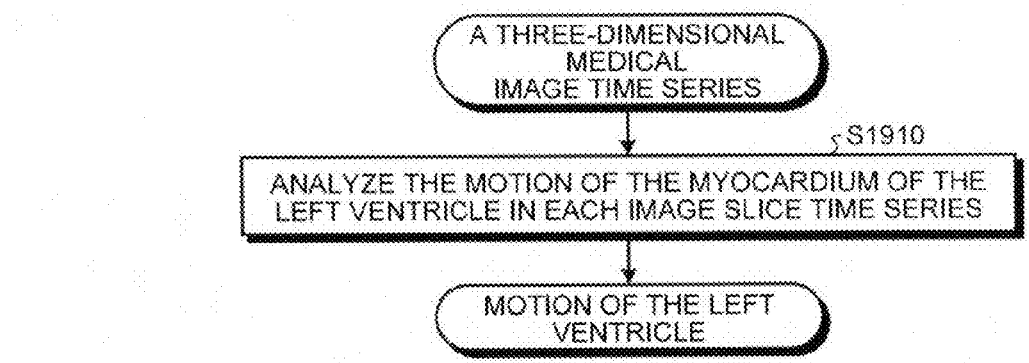
FIG. 19 is a schematic flow chart illustrating a myocardial motion analysis method according to another embodiment of the present invention.

FIG. 19 is a schematic flow chart illustrating a myocardial motion analysis method according to another embodiment of the present invention.

The myocardial motion analysis method according to the embodiment is used for analyzing the motion of the myocardium of a left ventricle in a three-dimensional medical image time series. The three-dimensional medical image time series includes a plurality of three-dimensional images that are acquired at a plurality of time points in a cardiac cycle. Each of the three-dimensional images consists of a plurality of parallel two-dimensional image slices that are intersected with the long axis of the left ventricle. The two-dimensional image slices located at the same location in the three-dimensional images form an image slice time series.

As shown in FIG. 19, in this method, in step S1910, the motion of the myocardium of the left ventricle is analyzed respectively in each medical image slice time series. Here, the motion of the myocardium of the left ventricle is analyzed in each medical image slice time series using the myocardial motion analysis method described in the part <3. Myocardial motion analysis method>. The motions of the myocardium in the plurality of two-dimensional image slices at the same time point form the motion of the left ventricle at this time point.

In addition, an image slice time series at a base part and an image slice time series at an apex part may be recognized from the three-dimensional medical image time series using any proper existing method. Then a myocardial motion analysis is only carried out on the image slice time series in a range defined by the image slice time series at the base and the image slice time series at the apex.

<5. Moving Object Contour Tracking Apparatus>

A moving object contour tracking apparatus according to embodiments of the present invention is described below with reference to FIG. 20-FIG. 26. The moving object contour tracking apparatus is configured to track a contour of a moving object which deforms periodically in an image slice time series. An image slice time series includes a plurality of image slices that are respectively acquired for the moving object at a plurality of time points in a motion period of the moving object. It should be appreciated that the moving object contour tracking apparatus according to the embodiments of the present invention can be used for tracking a contour of a moving object in various types of image slice time series. As an example but not a limitation, the image slice time series may be a medical image series formed by examinee data obtained through a medial diagnostic imaging device. The medial diagnostic device includes but is not limited to an X-ray imaging diagnostic device, an ultrasonic diagnostic imaging device, a computed tomography (CT) device, a magnetic resonance imaging (MRI) diagnostic device and a positron emission tomography (PET) device and the like.

Figure 20:
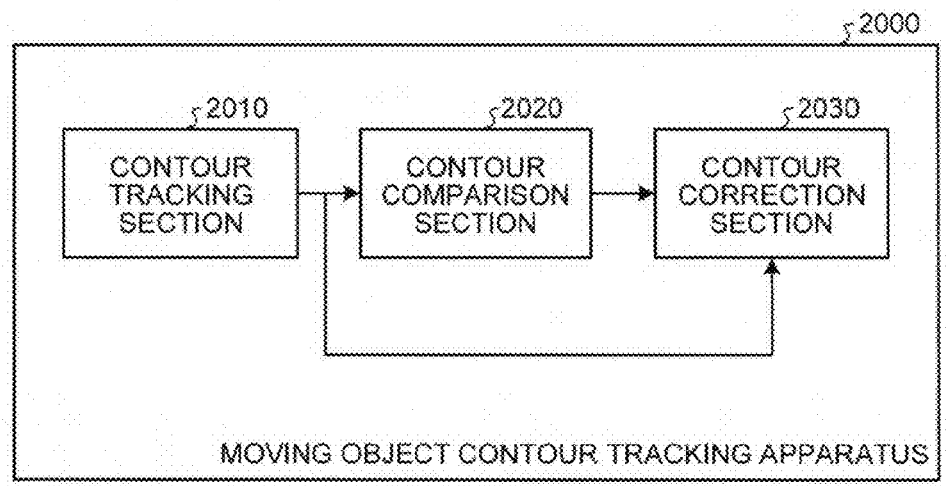
FIG. 20 is a schematic block diagram illustrating a moving object contour tracking apparatus according to an embodiment of the present invention.

FIG. 20 is a schematic block diagram illustrating a moving object contour tracking apparatus according to an embodiment of the present invention. As shown in FIG. 20, the moving object contour tracking apparatus 2000 includes a contour tracking section 2010, a contour comparison section 2020 and a contour correction section 2030. The contour tracking section 2010 is configured to perform, by taking an initial contour of the moving object in a predetermined image slice of the image slice time series as a starting contour, contour tracking in an image slice time series in a first time direction to acquire a first contour of the moving object in each image slice, wherein the last image slice in the first time direction is taken as the previous image slice of the first image slice; and to perform, by taking the initial contour as a starting contour, the contour tracking in the image slice time series in a second time direction to acquire a second contour of the moving object in each image slice, wherein the last image slice in the second time direction is taken as the previous image slice of the first image slice. The contour comparison section 2020 is configured to calculate a similarity between the first contour of the moving object in the predetermined image slice and the initial contour as a first similarity, and a second similarity between the second contour of the moving object in the predetermined image slice and the initial contour as a second similarity. The contour correction section 2030 is configured to take the contours in the image slices tracked by the contour tracking section 2010 in a contour tracking direction corresponding to a greater one of the first and second similarities as the contours of the moving object in the respective image slices.

In order to decrease the amount of calculation, according to another embodiment of the present invention, the contour tracking section 2010 may perform a turn of contour tracking at first, that is, to acquire the contour of the moving object in each image slice in one turn of contour tracking. The contour tracking section 2010 performs a second turn of contour tracking only when the contour comparison unit 2020 determines, based on the result of the first turn of contour tracking, that there may be an error in the first turn of contour tracking. The contour correction section 2030 corrects the result of the first turn of contour tracking with the result of the second contour tracking. The specific implementation mode may be understood by reference to related description of the moving object contour tracking method as described above and is therefore not repeated here.

Figure 21:
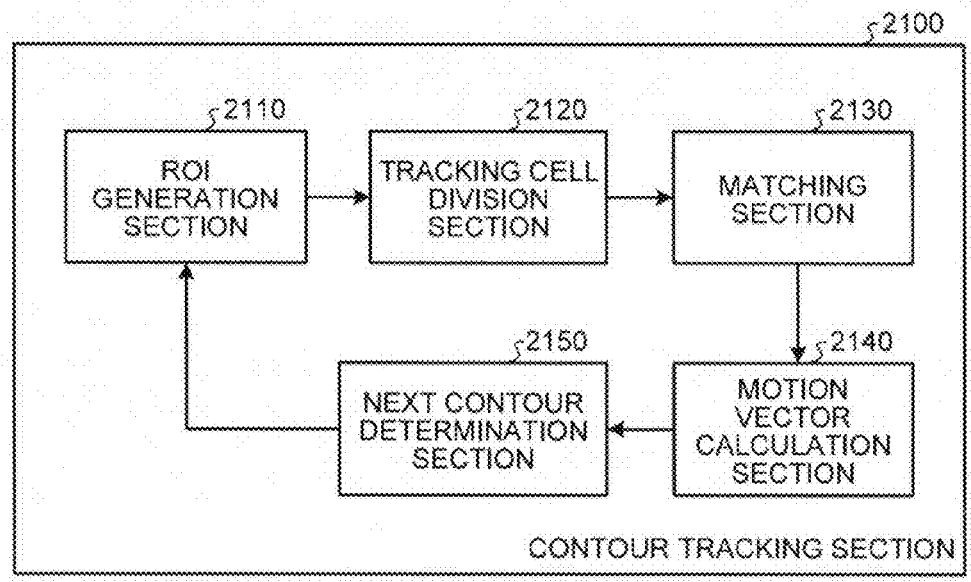
FIG. 21 is a schematic block diagram illustrating a contour tracking section according to an embodiment of the present invention.

In the moving object contour tracking apparatus according to the embodiments of the present invention, the contour tracking section 2010 may be realized using any proper existing method without limitation. As an example, FIG. 21 shows a schematic block diagram illustrating a contour tracking section according to an embodiment of the present invention. As shown in FIG. 21, the contour tracking section 2100 includes a region of interest (ROI) generation section 2110, a tracking cell division section 2120, a matching section 2130, a motion vector calculation section 2140 and a next contour determination section 2150. The ROI generation section 2110 is configured to expand the contour of the moving object in the current image slice to obtain a contour ROI. The tracking cell division section 2120 is configured to divide the contour ROI into a plurality of tracking cells with a predetermined size. The matching section 2130 is configured to perform template matching to obtain the locations of the plurality of tracking cells in the next image slice. The motion vector calculation section 2140 is configured to calculate the motion vectors of the plurality of tracking cells from the current image slice to the next image slice according to the locations of the plurality of tracking cells in the next image slice. The next contour determination section 2150 is configured to acquire the contour of the moving object in the next image slice based on the contour of the moving object in the current image slice and the motion vectors of the plurality of tracking cells from the current image slice to the next image slice.

The motion vector calculation section 2140 can use any proper method to calculate the motion vectors of the tracking cells. As a specific implementation mode, the motion vector calculation section 2140 is configured to calculate a weighted average of the motion vectors of the tracking cells within a predetermined range and adjacent to each contour point on the contour of the moving object in the current image slice, as the motion vector of the contour point from the current image slice to the next image slice. Accordingly, the next contour determination section 2150 may be configured to move the contour of the moving object in the current image slice according to the motion vector of each contour point on the contour of the moving object in the current image slice so as to acquire the contour of the moving object in the next image slice.

Figure 22:
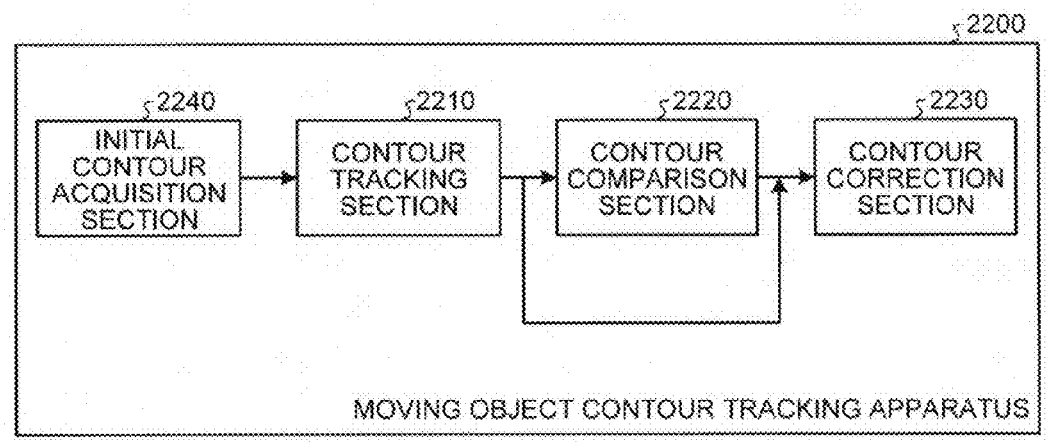
FIG. 22 is a schematic block diagram illustrating a moving object contour tracking apparatus according to another embodiment of the present invention.

In the moving object contour tracking apparatus according to the embodiments of the present invention, the initial contour of the moving object in the predetermined image slice may be acquired in advance or be acquired by the moving object contour tracking apparatus. FIG. 22 is a schematic block diagram illustrating a moving object contour tracking apparatus according to another embodiment of the present invention. In this embodiment, the moving object contour tracking apparatus 2200 includes an initial contour acquisition section 2240 for acquiring the initial contour of the moving object in a predetermined image slice.

In this embodiment, the moving object is a left ventricle, the image slice time series includes a plurality of image slices that are acquired with respect to a section of the left ventricle intersected with a long axis of the left ventricle at a plurality of time points in a cardiac cycle. The left ventricle has an endocardial contour and an epicardial contour. Therefore, the initial contour acquisition section 2240 may be configured to acquire an initial endocardial contour or an initial epicardial contour.

Figure 23:
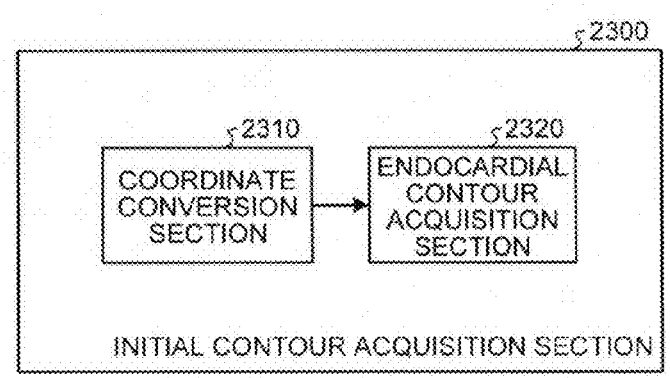
FIG. 23 is a schematic block diagram illustrating an initial contour acquisition section according to an embodiment of the present invention.

FIG. 23 is a schematic block diagram illustrating an initial contour acquisition section according to an embodiment of the present invention. As shown in FIG. 23, the initial contour acquisition section 2300 includes a coordinate conversion section 2310 and an endocardial contour acquisition section 2320. The coordinate conversion section 2310 is configured to convert the predetermined image slice to a polar coordinate system. The endocardial contour acquisition section 2320 is configured to acquire the endocardial contour of the left ventricle in the polar coordinate system. The coordinate conversion section 2310 is further configured to map the endocardial contour acquired by the endocardial contour acquisition section 2320 in the polar coordinate system to the original predetermined image slice.

Figure 24:
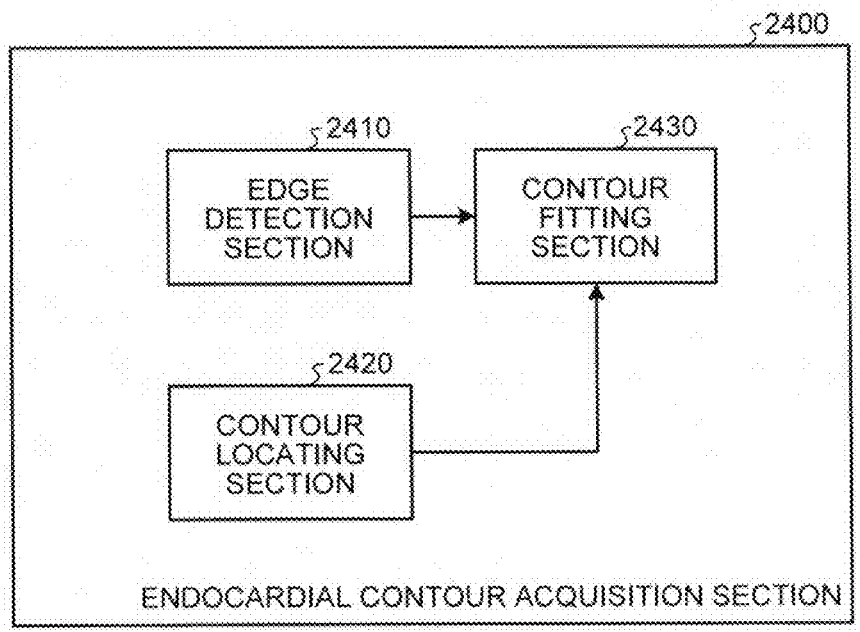
FIG. 24 is a schematic block diagram illustrating an endocardial contour acquisition section according to an embodiment of the present invention.

The endocardial contour acquisition section 2320 can acquire, in the polar coordinate system, the endocardial contour of the left ventricle in the predetermined image slice using any proper existing method. As an example, FIG. 24 is a schematic block diagram illustrating an endocardial contour acquisition section according to an embodiment of the present invention. In this embodiment, a rough location of the endocardial contour is determined in the polar coordinate system using a horizontal projection of an image slice, and then the endocardial contour is acquired from the edge image of the image slice using a straight line detection method. As shown in FIG. 24, the endocardial contour acquisition section 2400 includes an edge detection section 2410, a contour locating section 2420 and a contour fitting section 2430. The edge detection section 2410 is used for detecting edges in the predetermined image slice. The contour locating section 2420 is used for acquiring a radius of an endocardial contour of the left ventricle in the polar coordinate system using a horizontal projection of a gray scale image of the predetermined image slice. The contour fitting section 2430 is used for acquiring the endocardial contour of the left ventricle from the edges nearby the radius of the endocardial contour using a straight line detection method. As an example but not a limitation, the straight line detection method is a Hough transformation method.

Figure 25:
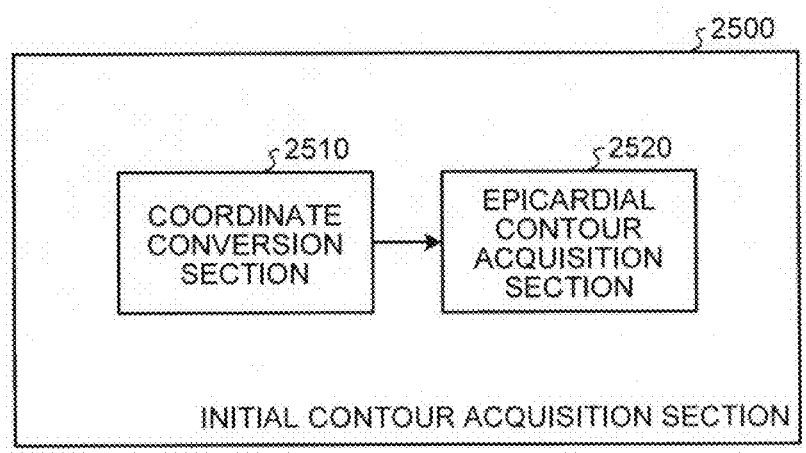
FIG. 25 is a schematic block diagram illustrating an initial contour acquisition section according to another embodiment of the present invention.

FIG. 25 is a schematic block diagram illustrating an initial contour acquisition section according to another embodiment of the present invention. As shown in FIG. 25, the initial contour acquisition section 2500 includes a coordinate conversion section 2510 and an epicardial contour acquisition section 2520. The coordinate conversion section 2510 is configured to convert a predetermined image slice into a polar coordinate system. The epicardial contour acquisition section 2520 is configured to acquire the epicardial contour of the left ventricle in the polar coordinate system. The coordinate conversion section 2510 is further configured to map the epicardial contour acquired by the epicardial contour acquisition section 2520 in the polar coordinate system into the original predetermined image slice.

Figure 26:
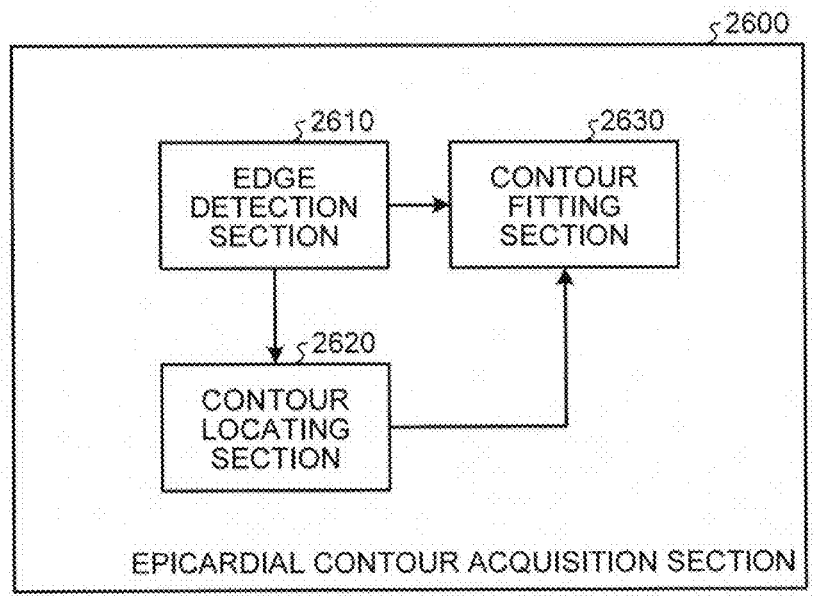
FIG. 26 shows a schematic block diagram illustrating an epicardial contour acquisition section according to an embodiment of the present invention.

The epicardial contour acquisition section 2520 can acquire, in the polar coordinate system, the epicardial contour of the left ventricle in the predetermined image slice using any proper existing method. As an example, FIG. 26 shows a schematic block diagram illustrating an epicardial contour acquisition section according to an embodiment of the present invention. As shown in FIG. 26, the epicardial contour acquisition section 2600 includes an edge detection section 2610, a contour locating section 2620 and a contour fitting section 2630. The edge detection section 2610 is configured to detect edges in the predetermined image slice. The contour locating section 2620 is configured to acquire, in the polar coordinate system, a radius of an endocardial contour of the left ventricle in the predetermined image slice using a horizontal projection of a gray scale image of the predetermined image slice, and to acquire a radius of an epicardial contour of the left ventricle in the predetermined image slice using the horizontal projection of an edge image of the predetermined image slice and the radius of the endocardial contour of the left ventricle. The contour fitting section 2630 is configured to acquire, in the polar coordinate system, the epicardial contour of the left ventricle from edges nearby the radius of the epicardial contour of the left ventricle using a curve fitting method. As an example but not a limitation, the curve fitting method is a least square method.

In accordance with another embodiment of the present invention, the moving object contour tracking apparatus may further include an interpolation determination section (not shown), which is configured to determine whether the time interval spanned by the image slice time series is shorter than the motion period of the moving object, and an interpolation execution section (not shown), which is configured to interpolate a compensation image slice into the image slice time series if the time interval spanned by the image slice time series is shorter than the motion period of the moving object, wherein the compensation image slice is predicted using an image interpolation method.

More detailed operations related to each section in the moving object contour tracking apparatus can be understood by reference to the description on the moving object contour tracking method in the above part <1. Moving object contour tracking method> and therefore is not described repeatedly here.

In the moving object contour tracking apparatus according to the embodiments of the present invention, the contour of the moving object is tracked in two time directions, and the tracking result with a higher reliability is taken as the contour of the moving object, thus improving the accuracy of the contour tracking. In addition, in the case where the moving object is a left ventricle, the endocardial contour and the epicardial contour of the left ventricle may be acquired accurately by converting the predetermined image slice to the polar coordinate system.

<6. Moving Object Contour Tracking Apparatus for a Three-Dimensional Image Time Series>

Figure 27:
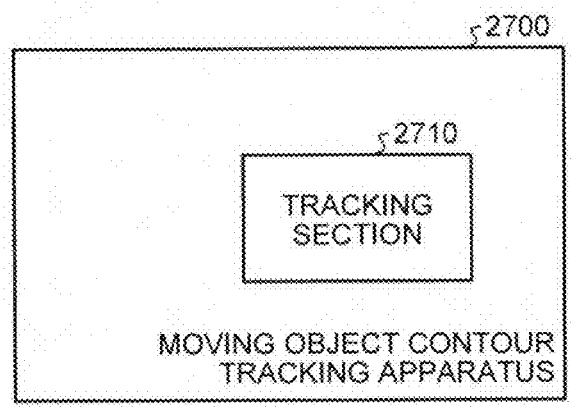
FIG. 27 is a schematic block diagram illustrating a moving object contour tracking apparatus according to another embodiment of the present invention.

FIG. 27 is a schematic block diagram illustrating a moving object contour tracking apparatus according to another embodiment of the present invention.

The moving object contour tracking apparatus according to this embodiment is configured to track the contour of a periodically deforming object in a three-dimensional image time series. The three-dimensional image time series includes a plurality of three-dimensional images that are acquired at a plurality of time points in a motion period of the moving object. Each of the three-dimensional images consists of a plurality of parallel two-dimensional image slices. The two-dimensional image slices located at the same location in the plurality of three-dimensional images form an image slice time series.

As shown in FIG. 27, the moving object contour tracking apparatus 2700 includes a tracking section 2710. The tracking section 2710 is configured to track the contour of the moving object in each image slice time series. Here, the tracking section 2710 may be implemented by the moving object contour tracking apparatus described in the above part <5. Moving object contour tracking apparatus>. The contours of the moving object in the plurality of two-dimensional image slices at the same time point form a three-dimensional contour of the moving object at this time point.

In addition, the moving object contour tracking apparatus 2700 may further include a control section (not shown), which inputs the image slice time series in the three-dimensional image time series into the tracking section 2710 one by one.

In addition, the moving object contour tracking apparatus 2700 may further include a limitation location recognizing device (not shown) for recognizing the image slice time series respectively corresponding to the two ends of the moving object from the three-dimensional image time series.

<7. Myocardial Motion Analysis Apparatus>

The myocardial motion analysis apparatus provided in embodiments of the present invention is described below with reference to FIG. 28-FIG. 31. The myocardial motion analysis apparatus is used for analyzing the motion of a myocardium of a left ventricle in a medical image slice time series. The image slice time series includes a plurality of image slices that are acquired with respect to a section of the left ventricle intersected with the long axis of the left ventricle at a plurality of time points in a cardiac cycle. In the myocardial motion analysis apparatus according to the embodiments of the present invention, a point linking pair is configured based on the motion correlation of an epicardial contour point and an endocardial contour point, and the motion of the myocardium is represented with the motion of the point linking pair.

Figure 28:
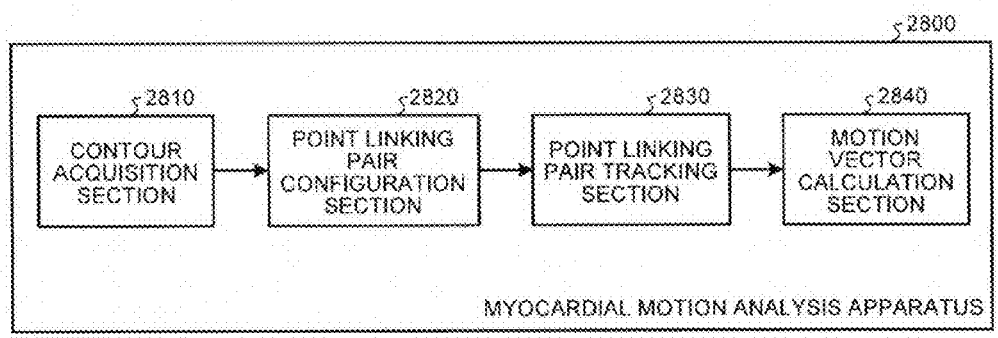
FIG. 28 is a schematic block diagram illustrating a myocardial motion analysis apparatus according to an embodiment of the present invention.

FIG. 28 is a schematic block diagram illustrating a myocardial motion analysis apparatus according to an embodiment of the present invention. As shown in FIG. 28, the myocardial motion analysis apparatus 2800 includes a contour acquisition section 2810, a point linking pair configuration section 2820, a point linking pair tracking section 2830 and a motion vector calculation section 2840.

In this embodiment, the contour acquisition section 2810 is configured to acquire the endocardial contour and the epicardial contour of the left ventricle in each image slice. The point linking pair configuration section 2820 is configured to configure the contour points on the endocardial contour and the epicardial contour in a reference image slice of the image slice time series as a plurality of point linking pairs, each point linking pair including a contour point on the endocardial contour and a contour point on the epicardial contour, and two contour points of each point linking pair being located on the same normal of a reference contour of a wall of the left ventricle in the reference image slice. The point linking pair tracking section 2830 is configured to determine the locations of each point linking pair in other image slices of the image slice time series than the predetermined image slice. The motion vector calculation section 2840 is configured to calculate, according to the locations of the plurality of point linking pairs in adjacent image slices of the image slice time series, a motion vector of a myocardium of the left ventricle between the adjacent image slices, wherein the myocardium is defined by the endocardial contour and the epicardial contour.

As an example, the reference contour may be the endocardial contour, the epicardial contour or a mean contour acquired from the endocardial contour and the epicardial contour.

According to another embodiment of the present invention, the motion vector calculation section 2840 is further configured to calculate the following motion components of the motion vector of the myocardium of the left ventricle between adjacent image slices: systole/diastole, circumferential expansion/contraction of the myocardium of the left ventricle, rotation of the myocardium of the left ventricle, and twist of the myocardium of the left ventricle. Specifically, the motion vector calculation section 2840 may calculate the aforementioned motion components using the motion component calculation method described in the part <3. Myocardial motion analysis method>.

The contour acquisition section 2810 can receive an endocardial contour and an epicardial contour that are manually marked in each image slice or acquire an endocardial contour and an epicardial contour using any proper existing method. As an example, the contour acquisition section 2810 can be implemented by the moving object contour tracking apparatus according to an embodiment of the present invention to acquire the endocardial contour and the epicardial contour of the left ventricle by taking the left ventricle as a moving object.

While acquiring the contour of the moving object, the moving object contour tracking apparatus according to the above embodiments also obtain continuous motion information of contour points of the moving object. According to another embodiment of the present invention, in the case where the contour acquisition section 2810 is implemented by the moving object contour tracking apparatus according to an embodiment of the present invention, the point linking pair tracking section 2830 is further configured to acquire the location of each endocardial contour point of the left ventricle in the next image slice based on the motion vector of the endocardial contour point from the current image slice to the next image slice, the left ventricle serving as a moving object; to acquire the location of each epicardial contour point of the left ventricle in the next image slice based on the motion vector of the epicardial contour point of the left ventricle in the current image slice from the current image slice to the next image slice, wherein the left ventricle serves as a moving object, and the motion vector of the epicardial contour point of the left ventricle is calculated by the motion vector calculation section 2140 of the moving object contour tracking apparatus; and to acquire the location of each point linking pair in the next image slice based on the locations of each endocardial contour point and each epicardial contour point in the next image slice.

Of course, the point linking pair tracking section 2830 may be directly implemented by the moving object contour tracking apparatus according to an embodiment of the present invention, and calculate the location of each endocardial contour point and the location of each epicardial contour point in the next image slice based on the motion vectors of the endocardial contour point and the epicardial contour point so as to determine the location of each point linking pair in the next image slice.

Figure 29:
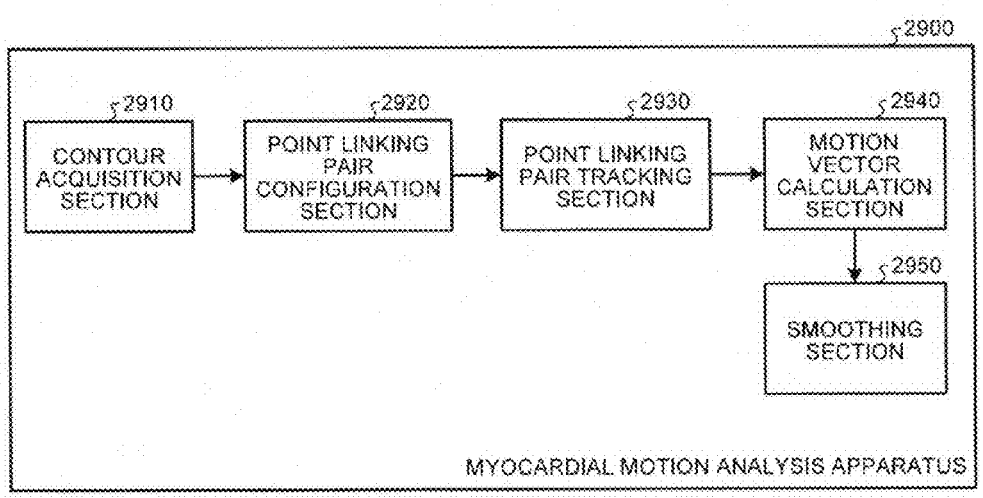
FIG. 29 is a schematic block diagram illustrating a myocardial motion analysis apparatus according to another embodiment of the present invention.

In an embodiment of the present invention, the respective motion components of the myocardium are smoothed to provide a more accurate motion vector consisting of the motion components of the myocardium, and consequentially, a more accurate myocardial motion analysis is provided. FIG. 29 is a schematic block diagram illustrating a myocardial motion analysis apparatus according to another embodiment of the present invention. As shown in FIG. 29, the myocardial motion analysis apparatus 2900 includes a contour acquisition section 2910, a point linking pair configuration section 2920, a point linking pair tracking section 2930, a motion vector calculation section 2940 and a smoothing section 2950. The contour acquisition section 2910, the point linking pair configuration section 2920, the point linking pair tracking section 2930 and the motion vector calculation section 2940 are respectively identical to the contour acquisition section 2810, the point linking pair configuration section 2820, the point linking pair tracking section 2830 and the motion vector calculation section 2840 shown in FIG. 28 in structure and function. The smoothing section 2950 is configured to smooth motion component time series which are constructed by the respective motion components of the motion vector of the myocardium of the left ventricle between adjacent image slices.

Figure 30:
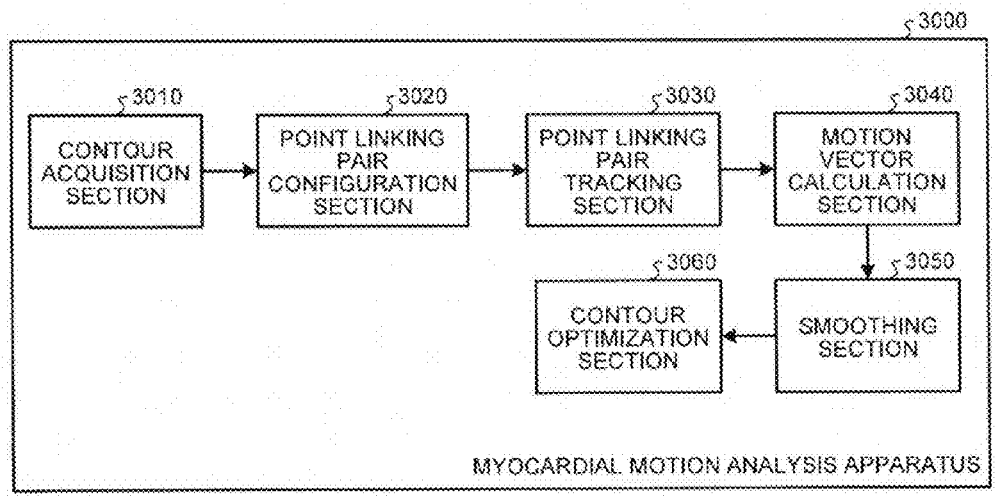
FIG. 30 is a schematic block diagram illustrating a myocardial motion analysis apparatus according to still another embodiment of the present invention.

FIG. 30 is a schematic block diagram illustrating a myocardial motion analysis apparatus according to another embodiment of the present invention. In this embodiment, the myocardial motion analysis apparatus 3000 includes a contour acquisition section 3010, a point linking pair configuration section 3020, a point linking pair tracking section 3030, a motion vector calculation section 3040 and a smoothing section 3050, which are respectively identical to the contour acquisition section 2910, the point linking pair configuration section 2920, the point linking pair tracking section 2930, the motion vector calculation section 2940 and the smoothing section 2950 shown in FIG. 29 in structure and function. In addition, the myocardial motion analysis apparatus 3000 further includes a contour optimization section 3060, which is configured to acquire, based on the endocardial contour and the epicardial contour of the left ventricle in a reference image slice, a new endocardial contour and a new epicardial contour of the left ventricle in each of the other image slices of the image slice time series by using the smoothed motion component time series of the myocardium of the left ventricle between adjacent image slices, thereby providing a more accurate endocardial contour and epicardial contour.

Figure 31:
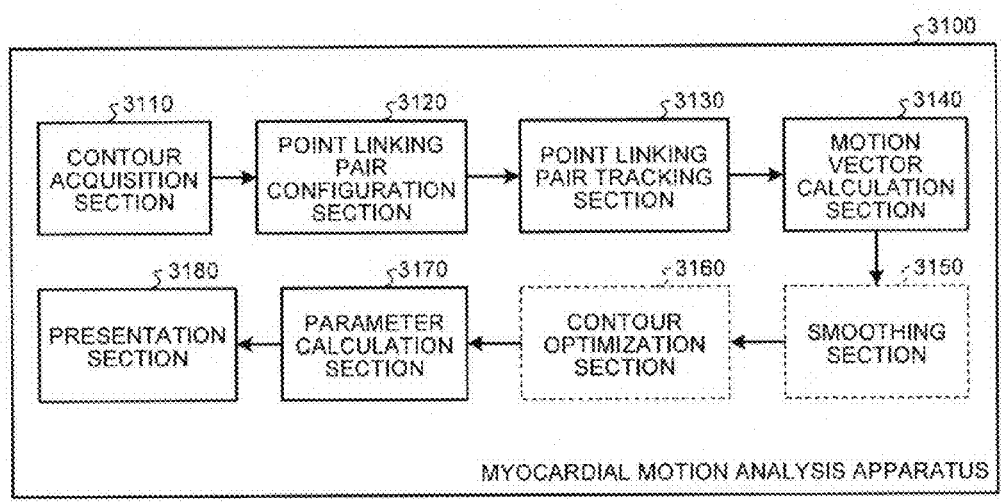
FIG. 31 is a schematic block diagram illustrating a myocardial motion analysis apparatus according to yet another embodiment of the present invention.

FIG. 31 is a schematic block diagram illustrating a myocardial motion analysis apparatus according to another embodiment of the present invention. In this embodiment, in addition to including a contour acquisition section 3110, a point linking pair configuration section 3120, a point linking pair tracking section 3130 and a motion vector calculation section 3140 which are identical to those in the myocardial motion analysis apparatus shown in FIG. 28, the myocardial motion analysis apparatus 3100 further includes a parameter calculation section 3170 and a presentation section 3180. The parameter calculation section 3170 is configured to calculate a strain of the myocardium of the left ventricle according to the motion vector of the myocardium of the left ventricle between adjacent image slices. The presentation section 3180 is configured to present the strain of the myocardium of the left ventricle on a corresponding original image slice.

In addition, preferably, the myocardial motion analysis apparatus 3100 may further include a smoothing section 3150 and/or a contour optimization section 3160. The smoothing section 3150 is identical to the smoothing section 2950 shown in FIG. 29 in structure and function.

More detailed operations related to each section in the myocardial motion analysis apparatus can be understood by reference to the description given in the part <3. Myocardial motion analysis method> on the myocardial motion analysis method, and is therefore not described repeatedly here.

The myocardial motion analysis apparatus according to the embodiments of the present invention adds constraints by representing the motion of the myocardium with the motion of the point linking pairs, and therefore can analyze the motion of the myocardium more stably. In addition, the motion of the myocardium can be comprehensively analyzed by resolving the motion vector of the myocardium into motion components such as the systole/diastole, the circumferential expansion/contraction, the rotation and the twist. In addition, the motion components of the myocardium are smoothed to provide a more accurate motion vector consisting of the motion components of the myocardium, thereby providing a more accurate myocardial motion analysis. The endocardial contour and the epicardial contour are re-acquired based on the smoothed motion vector, and thus the re-acquired contours are more accurate.

<8. Myocardial Motion Analysis Apparatus for a Three-Dimensional Medical Image Time Series>

Figure 32:
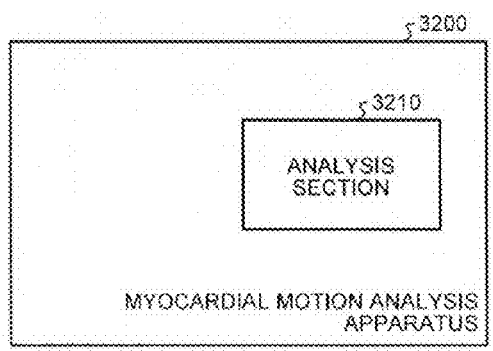
FIG. 32 is a schematic block diagram illustrating a myocardial motion analysis apparatus according to a further embodiment of the present invention.

FIG. 32 is a schematic block diagram illustrating a myocardial motion analysis apparatus according to a further embodiment of the present invention.

The myocardial motion analysis apparatus according to this embodiment is used for analyzing the motion of the myocardium of a left ventricle in a three-dimensional medical image time series. The three-dimensional medical image time series includes a plurality of three-dimensional images that are acquired at a plurality of time points in a cardiac cycle. Each of the three-dimensional images consists of a plurality of parallel two-dimensional image slices that are intersected with the long axis of the left ventricle. The two-dimensional image slices located at the same location in the three-dimensional images form an image slice time series.

As shown in FIG. 32, the myocardial motion analysis apparatus 3200 includes an analysis section 3210, which is configured to analyze the motion of the myocardium of the left ventricle in each medical image slice time series. Here, the analysis section 3210 may be implemented by the myocardial motion analysis apparatus described in the part <7. Myocardial motion analysis apparatus>. The motions of the myocardium in the plurality of two-dimensional image slices at the same time point form a motion of the left ventricle at this time point.

In addition, the myocardial motion analysis apparatus 3200 may include a control section (not shown), which inputs the image slice time series in the three-dimensional medical image time series into the analysis section 3210 one by one.

In addition, the myocardial motion analysis apparatus 3200 may further include a limitation location recognizing device (not shown), which is configured to recognize the image slice time series at a base part and the image slice time series at an apex part from the three-dimensional medical image time series.

<9. Computer Structure Capable of Implementing the Methods/Apparatuses Disclosed in the Embodiments of the Preset Invention>

As an example, the respective steps of the above-described moving object contour tracking method and myocardial motion analysis method and the respective sections, modules and/or units of the above-described moving object contour tracking apparatus and myocardial motion analysis apparatus may be implemented as software, firmware, hardware or the combination thereof in a medical diagnostic apparatus (e.g. X-ray diagnostic device, UL diagnostic device, CT device, MRI diagnostic device or PET device), and serve as a part of the medical diagnostic apparatus. As an example, the above-described methods and/or apparatuses may be implemented in an existing medical diagnostic device by making some modification on the sections of the existing medical diagnostic device. As another example, the respective steps of the above-described methods and the respective sections, modules and/or units of the above-described apparatuses may be implemented as an apparatus separately from the above-described medical diagnostic apparatus. The specific means or approaches that may be used in configuring the sections, modules and units in the foregoing apparatuses through software, firmware, hardware or any combination thereof are well known to those skilled in the art and therefore will not be repeatedly described.

As an example, the steps of the above-described methods and the sections, modules and/or units of the above-described apparatuses may be implemented as software, firmware, hardware or any combination thereof. In the case where the steps of the above-described methods and the sections, modules and/or units of the above-described apparatuses are implemented through software or firmware, a software program constituting the software for realizing the above-described methods may be installed in a computer (e.g. the general computer 3300 shown in FIG. 33) with a specific hardware structure from a storage medium or a network, and the computer, when installed with various programs, is capable of perform various functions.

Figure 33:
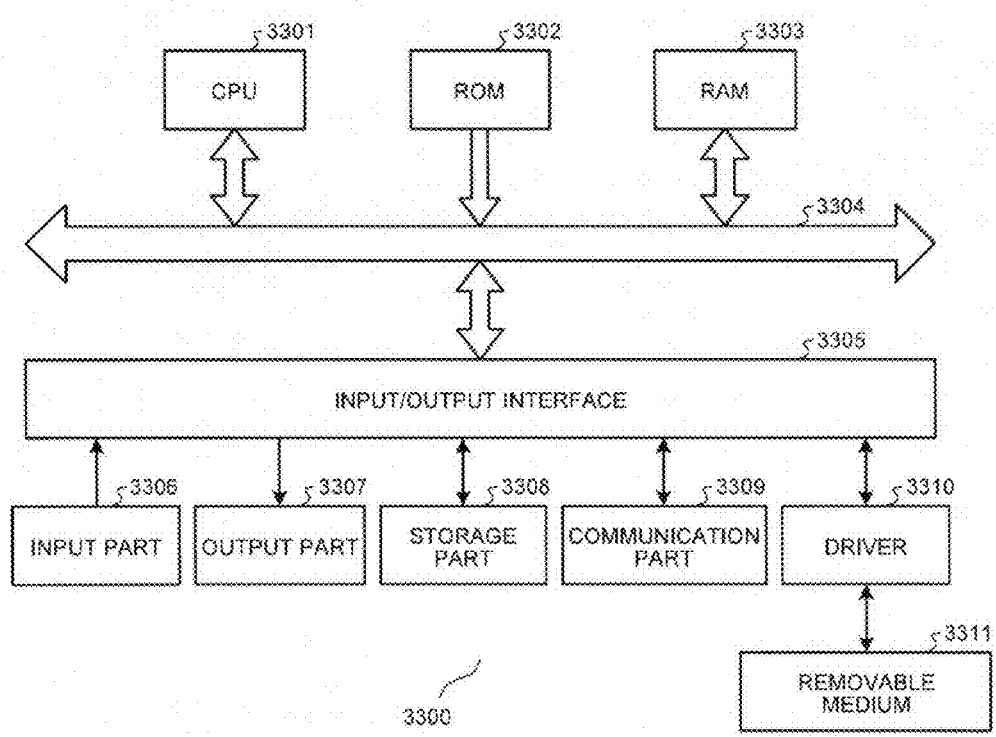
FIG. 33 shows a computer structure capable of implementing the methods/apparatuses disclosed in the embodiments of the preset invention.

In FIG. 33, a central processing unit (CPU) 3301 executes various processes according to the programs stored in a read-only memory (ROM) 3302 or programs loaded to a random access memory (RAM) 3303 from a storage part 3308. Data needed by the CPU 3301 to execute the various processes are also stored in the RAM 3303 as required. The CPU 3301, the ROM 3302 and the RAM 3303 are connected with each other via a bus 3304. An input/output interface 3305 is also connected to the bus 3304.

The following parts are connected to the input/output (I/O) interface 3305: an input part 3306 (including a keyboard, a mouse and etc.), an output part 3307 (including a display such as a cathode-ray tube (CRT) or a liquid crystal display (LCD), and a speaker, etc.), the storage part 3308 (including a hard disk, etc.), and a communication part 3309 (including a network interface card such as an LAN card, a MODEM and etc.). The communication part 3309 executes communication processing via a network such as the Internet. A driver 3310 can also be connected to the input/output interface 3305 as required. A removable medium 3311 such as a magnetic disk, an optical disk, a magneto-optical disk or a semiconductor memory can be mounted on the driver 3310 as required, such that the computer program read out therefrom is installed into the storage part 3308 as required.

In the case that the above series of processes are implemented by software, a program constituting the software is installed from a network such as the Internet or from a storage medium such as the removable medium 3311.

It is to be understood by those skilled in the art that such storage medium is not limited to the removable medium 3311 storing programs therein and distributing the programs to a user(s) dependently from a device. Examples of the removable medium 3311 include a magnetic disk (including a Floppy Disk (FD) (registered trademark)), an optical disk (including a Compact Disk-Read Only Memory (CD-ROM) and a Digital Versatile Disc (DVD)), a magneto-optical disk (including a Microdisk (MD) (registered trademark)) and a semiconductor memory. Alternatively, the storage medium can be the ROM 3302, a hard disk contained in the storage part 3308, etc., in which programs are stored and which is distributed to a user(s) along with a device the storage medium is contained in.

The present invention further provides a program product in which computer-readable instruction codes are stored. The instruction codes, when read and executed by a machine, can execute the methods according to the embodiments of the present invention.

Correspondingly, the storage medium for carrying the program product storing machine-readable instruction codes is also incorporated in the disclosure of the present invention. The storage medium includes, but is not limited to, a flexible disk, an optical disk, a magneto-optical disk, a storage card and a storage stick.

In the above description of the specific embodiments of the present invention, features described and/or illustrated with respect to one embodiment can be used in one or more other embodiments in an identical or similar manner, be combined with features in other embodiments, or replace features in other embodiments.

It should be emphasized that, the term "comprise/include", as used in the present description, refers to the presence of features, sections, steps or components, but does not exclude the presence or addition of one or more other features, sections, steps or components.

In the above embodiments and examples, the steps and/or units are represented with a reference sign consisting of numbers. It should be understood by those of ordinary skill of the art that the reference signs are merely intended to facilitate description and drawing depiction, but are not to be construed as indicating the orders of the steps and/or units nor a limitation on any other aspect.

Furthermore, the methods of the present invention are not limited to being executed in the temporal orders as described in the specification, but can also be executed in other temporal order, in parallel or separately. Therefore, the execution orders of the methods described in the present specification do not constitute limitation to the technical scope of the present invention.

Although the present invention has been disclosed with reference to descriptions for the specific embodiments of the present invention, it should be understood that all of the above mentioned embodiments and examples are illustrative instead of limiting. Those skilled in the art can devise various modifications, improvements or equivalents for the present invention, within the spirit and scope of the appended claims. The modifications, improvements or equivalents should also be considered as being included in the protection scope of the present invention.

What is claimed is:

1. A moving object contour tracking apparatus for tracking a contour of a periodically deforming object in an image slice time series, the image slice time series comprising a plurality of image slices acquired at a plurality of time points in a motion period of the moving object, the moving object contour tracking apparatus comprising:

a contour tracking section configured to
  perform, by taking an initial contour of the moving object in a predetermined image slice of the image slice time series as a starting contour, contour tracking in the image slice time series in a first time direction to acquire a first contour of the moving object in each image slice of the image slice time series, and
  perform, by taking the initial contour as a starting contour, contour tracking in the image slice time series in a second time direction to acquire a second contour of the moving object in each image slice of the image slice time series;
a contour comparison section configured to calculate a similarity between the first contour of the moving object in the predetermined image slice and the initial contour as a first similarity and a similarity between the second contour of the moving object in the predetermined image slice and the initial contour as a second similarity; and
a contour correction section configured to take the contours in the image slices tracked by the contour tracking section in a contour tracking direction corresponding to a greater one of the first and second similarities as the contours of the moving object in the respective image slices.

2. The apparatus according to claim 1, wherein the contour tracking section comprises:
  a region of interest (ROI) generation section configured to expand a contour of the moving object in a current image slice to obtain a contour ROI;
  a tracking cell division section configured to divide the contour ROI into a plurality of tracking cells with a predetermined size;
  a matching section configured to perform template matching to obtain locations of the plurality of tracking cells in the next image slice;
  a motion vector calculation section configured to calculate motion vectors of the plurality of tracking cells from the current image slice to a next image slice according to the locations of the plurality of tracking cells in the next image slice; and
  a next contour determination section configured to acquire a contour of the moving object in the next image slice based on the contour of the moving object in the current image slice and the motion vectors of the plurality of tracking cells from the current image slice to the next image slice.

3. The apparatus according to claim 2, wherein
  the motion vector calculation section is further configured to calculate a weighted average of the motion vectors of the tracking cells within a predetermined range and adjacent to each contour point on the contour of the moving object in the current image slice as a motion vector of the contour point from the current image slice to the next image slice; and
  the next contour determination section is further configured to move the contour of the moving object in the current image slice according to the motion vector of each contour point on the contour of the moving object in the current image slice so as to acquire the contour of the moving object in the next image slice.

4. The apparatus according to claim 1, wherein the moving object is a left ventricle, the image slice time series comprises a plurality of image slices that are acquired with respect to a section of the left ventricle intersected with a long axis of the left ventricle at a plurality of time points in a cardiac cycle, and the apparatus further comprises an initial contour acquisition section comprising:
  a coordinate conversion section configured to convert the predetermined image slice to a polar coordinate system and map an endocardial contour of the left ventricle acquired by an endocardial contour acquisition section in the polar coordinate system to the original predetermined image slice as the initial contour; and
  the endocardial contour acquisition section configured to acquire the endocardial contour of the left ventricle in the polar coordinate system.

5. The apparatus according to claim 4, wherein the endocardial contour acquisition section comprises:
  an edge detection section configured to detect edges in the predetermined image slice;
  a contour locating section configured to acquire, in the polar coordinate system, a radius of the endocardial contour of the left ventricle in the predetermined image slice using a horizontal projection of a gray scale image of the predetermined image slice; and
  a contour fitting section configured to acquire, in the polar coordinate system, the endocardial contour of the left ventricle from the edges nearby the radius of the endocardial contour of the left ventricle using a straight line detection method.

6. The apparatus according to claim 1, wherein the moving object is a left ventricle, the image slice time series comprises a plurality of image slices acquired with respect to a section of the left ventricle intersected with a long axis of the left ventricle at a plurality of time points in a cardiac cycle, and the apparatus further comprises an initial contour acquisition section comprising:
  a coordinate conversion section configured to convert the predetermined image slice to a polar coordinate system and map an epicardial contour of the left ventricle acquired by an epicardial contour acquisition section in the polar coordinate system to the original predetermined image slice as the initial contour; and
  the epicardial contour acquisition section configured to acquire the epicardial contour of the left ventricle in the polar coordinate system.

7. The apparatus according to claim 6, wherein the epicardial contour acquisition section comprises:
  an edge detection section configured to detect edges in the predetermined image slice;
  a contour locating section configured to acquire, in the polar coordinate system, a radius of an endocardial contour of the left ventricle in the predetermined image slice using a horizontal projection of a gray scale image of the predetermined image slice, and to acquire a radius of the epicardial contour of the left ventricle in the predetermined image slice using a horizontal projection of an edge image of the predetermined image slice and the radius of the endocardial contour of the left ventricle; and
  a contour fitting section configured to acquire, in the polar coordinate system, the epicardial contour of the left ventricle from the edges nearby the radius of the epicardial contour of the left ventricle using a curve fitting method.

8. The apparatus according to claim 1, further comprising:
  an interpolation determination section configured to determine whether a time interval spanned by the image slice time series is shorter than the motion period of the moving object; and
  an interpolation execution section configured to interpolate a compensation image slice into the image slice time series if the time interval spanned by the image slice time series is shorter than the motion period of the moving object, wherein the compensation image slice is predicted using an image interpolation method.

9. The apparatus according to claim 1, wherein the image slice time series is a medical image series formed by data acquired by a medical diagnostic apparatus.

10. A moving object contour tracking apparatus for tracking a contour of a periodically deforming moving object in a three-dimensional image time series, the three-dimensional image time series comprising a plurality of three-dimensional images acquired at a plurality of time points in a motion period of the moving object, each of the three-dimensional images consisting of a plurality of parallel two-dimensional image slices, and the two-dimensional image slices located at the same location in the plurality of three-dimensional images forming an image slice time series, the apparatus comprising:
 a tracking section implemented by the moving object contour tracking apparatus according to any one of claims 1-9, and configured to track a contour of the moving object in each image slice time series,
 wherein the contours of the moving object in the plurality of two-dimensional image slices at the same time point form a three-dimensional contour of the moving object at this time point.

11. A moving object contour tracking method for tracking a contour of a periodically deforming object in an image slice time series, the image slice time series comprising a plurality of image slices acquired at a plurality of time points in a motion period of the moving object, the method comprising:
 performing, by taking an initial contour of the moving object in a predetermined image slice of the image slice time series as a starting contour, contour tracking in the image slice time series in a first time direction to acquire a first contour of the moving object in each image slice of the image slice time series;
 performing, by taking the initial contour as a starting contour, contour tracking in the image slice time series in a second time direction to acquire a second contour of the moving object in each image slice of the image slice time series;
 calculating a similarity between the first contour of the moving object in the predetermined image slice and the initial contour as a first similarity and a similarity between the second contour of the moving object in the predetermined image slice and the initial contour as a second similarity; and
 taking the contours in the image slices tracked by the contour tracking section in a contour tracking direction corresponding to a greater one of the first and second similarities as the contours of the moving object in the respective image slices.

* * * * *